(12) United States Patent
Epstein et al.

(10) Patent No.: US 9,127,273 B2
(45) Date of Patent: Sep. 8, 2015

(54) UNC-45A SPLICE VARIANTS BASED CANCER DIAGNOSTICS AND THERAPEUTICS

(75) Inventors: Henry Fredric Epstein, Bellaire, TX (US); Wei Guo, Galveston, TX (US); Daisi Chen, Galveston, TX (US); Ram Singh, Lubbock, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 302 days.

(21) Appl. No.: 13/144,476

(22) PCT Filed: Jan. 12, 2010

(86) PCT No.: PCT/US2010/020764
§ 371 (c)(1), (2), (4) Date: Jul. 13, 2011

(87) PCT Pub. No.: WO2010/083162
PCT Pub. Date: Jul. 22, 2010

(65) Prior Publication Data
US 2012/0135408 A1     May 31, 2012

Related U.S. Application Data

(60) Provisional application No. 61/144,296, filed on Jan. 13, 2009.

(51) Int. Cl.
    *C07H 21/04*     (2006.01)
    *C12N 15/113*     (2010.01)
    *C07K 14/47*     (2006.01)
    *G01N 33/574*     (2006.01)

(52) U.S. Cl.
CPC .............. *C12N 15/113* (2013.01); *C07K 14/47* (2013.01); *G01N 33/574* (2013.01); *C12N 2310/14* (2013.01); *C12N 2310/531* (2013.01)

(58) Field of Classification Search
None
See application file for complete search history.

(56) References Cited

U.S. PATENT DOCUMENTS 7,691,997 B2 * 4/2010 Khvorova et al. ........... 536/24.5

OTHER PUBLICATIONS

Bazzaro et al., 2007, Am J Pathol 171(5):1640-1649.
GenBank: AK125721.1, Jul. 3, 2008 <URL: http://www.ncbi.nlm.nih.gov/nuccore/34531911>.
NCBI Reference Sequence: NM_018671.2, Jul. 3, 2010 <http://www.ncbi.nlm.nih.gov/nuccore/34531911>.
Price et al., 2002, J Cell Sci 115(21):4103-23.
Epstein et al. International Search Report and Written Opinion, PCT/US2010/020764, Jul. 13, 2010.
Guo et al., "Differential Turnover of Myosin Chaperone UNC-45A Isoforms Increases in Metastatic Human Breast Cancer" J. Mol. Biol. (2011).

* cited by examiner

*Primary Examiner* — Kimberly Chong
(74) *Attorney, Agent, or Firm* — Norton Rose Fulbright US LLP

(57) ABSTRACT

Methods and compositions to diagnose and treat cancers using UNC-45A splice variants are disclosed. Expression of a human UNC-45A929 splice variant that is shorter than UNC-45A944 splice variant is increased in cancer cells including metastatic cancers. siRNA to inhibit or downregulate UNC-45A splice variants in cancers are disclosed.

10 Claims, 5 Drawing Sheets

UNC-45A 929:
sense sequence UGGCCGUCACUACCCUGGUUUCUUU (SEQ ID NO:9)

antisense sequence AAAGAAACCAGGGUAGUGACGGCCA (SEQ ID NO:10)

UNC-45A 944:
sense sequence GGUCCAGGGACCCCCGAGCCCCG (SEQ ID NO:11)

antisense sequence CGGGGCUCGGGGGUCCCUGGACC (SEQ ID NO:12)

UNC-45A SPLICE VARIANTS BASED CANCER DIAGNOSTICS AND THERAPEUTICS

This application claims priority to U.S. provisional application No. 61/144,296, filed Jan. 13, 2009, the content of which is herein incorporated by reference in its entirety.

BACKGROUND

The present disclosure relates to UNC-45A splice variants and their use in cancer therapeutics and diagnostics.

Approximately 90% of breast cancer deaths are caused by metastasis to bones, liver, lungs, or brain with a survival time for patients of 2 years. Cancer metastasis is tightly related to cell motility including cell invasion and migration in breast cancer.

UNC-45 functions as a molecular chaperone for myosin motors and as a co-chaperone for Hsp90 in both vertebrate and invertebrate animals. Myosins are actin-based motors that play critical roles in a variety of cellular processes, including cytokinesis, cellular trafficking, phagocytosis, maintenance of cell shape, and muscle contraction. Myosin-based movement results from a specific cycle of the myosin head binding and releasing ATP and actin. During this process, the myosin head goes through multiple folding conformations. Evidence from a variety of experimental systems indicates that myosins use specialized chaperones during their activity, folding, and assembly.

Molecular chaperones are necessary for de novo folding and structural maintenance of the myosin head. Expression of the myosin motor domain in bacteria results in misfolding. In vertebrate systems, the chaperonin containing TCP-1 (CCT), as well as molecular chaperones Hsp90 and Hsc70, are necessary but not sufficient in the folding of striated muscle myosin.

The UNC-45 family of molecular chaperones is necessary for the proper functions of myosins, the motor proteins of the actin cytoskeleton and the contractile thick filaments of the muscle and heart. In humans and other vertebrates, two genes have been discovered which encode UNC-45 chaperones. One encodes UNC-45A that is essential for embryonic development, cell migration, and cell division because of its role in the activation of both myosin IIA (MYH9) and Myosin IIB (MyH10). UNC-45A or its mouse ortholog UNC-45a is necessary for cell proliferation in mouse myoblasts and for cell migration and proliferation in metastatic human ovarian cancer cells.

Mutations in UNC-45/Cro1p/She4p(Dim1p) domain (UCS) proteins result in phenotypes related to defects in myosin folding and assembly. Reduced UCS domain protein function in fungal mutants produces myosins defective in actin:ATP transduction. In *Caenorhabditis elegans*, null unc-45 alleles results in embryonic arrest of body wall muscle development, and temperature-sensitive mutations lead to a paralyzed or uncoordinated phenotype at the restrictive temperature with marked disorganization of myofibrils. UNC-45 exerts chaperone activity in vitro on the myosin head and acts as a cochaperone that specifically binds Hsp90.

Mice and humans each have two genes that are located on different chromosomes, which encode distinct UNC-45-like protein isoforms, and are expressed either in multiple tissues or only in cardiac and skeletal muscles. Their expression is regulated during muscle differentiation in vitro, with the striated muscle isoform mRNA appearing during myoblast fusion.

UNC-45 is a substrate of an E3/E4-multiubiquitination complex containing CHN-1 (the *C. elegans* homologue of CHIP) and UFD-2. chn-1-null worms are viable and appear morphologically normal. However, UNC-45 overexpression leads to an uncoordinated phenotype in these worms, suggesting that increased levels of UNC-45 may cause muscle defects.

RNA interference (RNAi) pathway is often used in experimental biology to study the function of genes in a variety of in vitro and in vivo model systems. Double-stranded RNA is synthesized with a sequence complementary to a gene of interest and introduced into a cell or organism, where it is recognized as exogenous genetic material and activates the RNAi pathway. Using this mechanism, researchers induce a drastic decrease in the expression of a targeted gene. Since RNAi may not totally eliminate the expression of the target gene, this technique is sometimes referred as a "knockdown", to distinguish it from "knockout" procedures in which expression of a gene is entirely eliminated.

SUMMARY

Methods and compositions to selectively suppress or down regulate the 929 amino acid residue splice variant of UNC-45A are disclosed. Agents including short/small interfering RNAs (siRNA) and short/small hairpin RNAs (shRNA) that specifically target the 929 residue splice variant (hereinafter "UNC-45A929") are disclosed.

Methods and compositions to diagnose cancer based on the expression level of the UNC-45A929 splice variant are also disclosed. For example, the 929 residue splice variant of UNC-45A is elevated in several cancers including breast, cervical and ovarian, when compared to the 944 splice variant. In addition, the mRNA for the 929 splice variant has unique sequences in its 5' untranslated region compared to the 944 splice variant. These differences also permit design of nucleic acid sequences that specifically target UNC-45A929 splice variant.

In an aspect, shRNA and siRNA sequences are designed to selectively downregulate (e.g., knockdown) UNC-45A929 mRNA and protein when compared to the 944 residue splice variant UNC-45A mRNA and protein. These UNC-45A929 specific reagents have therapeutic uses. Any cancer type that has the UNC-45A929 expressed to a greater level than the 944 residue splice variant is capable of being treated by the methods and compositions disclosed herein.

A short interfering RNA (siRNA) or a short hairpin RNA (shRNA) molecule for selectively reducing the expression of a human UNC-45A splice variant in a cell, wherein the RNA molecule is substantially complementary to at least a part of a mRNA encoding the splice variant, wherein the splice variant comprises a nucleic acid sequence as in SEQ ID NO: 1 (nucleotide positions 1-835) or SEQ ID NO: 2.

In an aspect, the siRNA targets TGGCCGTCACTAC-CCTGGTTTCTTT (SEQ ID NO:5) or GGACAGAGGTGG-TAGTGAACT (SEQ ID NO:6) of the UNC-45A929 splice variant. In an aspect, the siRNA targets GGTCCAGGGAC-CCCCGAGCCCCG (SEQ ID NO:7) or GTGAGTGGTC-CAGGGACCCC (SEQ ID NO:8) of UNC-45A944.

A pharmaceutical composition includes an effective amount of a siRNA or shRNA that specifically inhibits the expression of a human UNC-45A929 splice variant in a cancer cell. In an aspect, the pharmaceutical composition contains the siRNA that includes one or more modified nucleotides. In an aspect, the shRNA is expressed from a vector.

A method of reducing the proliferation of a cancer cell includes contacting the cancer cell with an RNAi agent that specifically downregulates the expression of UNC-45A splice variants. In an aspect, the RNAi agent is a siRNA molecule that specifically targets UNC-45A929 splice variant.

In an aspect, the cancer cell is selected from the group consisting of breast cancer, cervical cancer and colon cancer. In an aspect, the cancer cell is a metastatic breast cancer cell.

A method of diagnosing a malignant or a pre-malignant cell includes determining that the cell is malignant or pre-malignant based on the increased expression level of one or more UNC-45A splice variants in the malignant or pre-malignant cell as compared to a non-cancerous cell.

In an aspect, the expression level is determined by reverse transcriptase (RT)-PCR or determined by immunohistochemistry.

In an aspect, the expression level of the UNC-45A splice variant is determined RNA expression or protein levels.

In an aspect, the expression level is determined in a tissue sample.

A method of diagnosing whether a subject has cancer includes determining the expression of a splice variant UNC-45A929 in an isolated sample, wherein the UNC-45A929 splice variant includes an untranslated nucleotide sequence of 1-835 of SEQ ID NO: 1.

In an aspect, the expression level of the UNC-45A929 splice variant is determined in the isolated tissue by the RNA levels of UNC-45A929.

In an aspect, the expression level of the UNC-45A929 splice variant is determined in the isolated tissue by the protein or peptide levels of UNC-45A929.

In an aspect, the expression levels of the splice variant UNC-45A929 is higher than the expression levels of a splice variant UNC-45A944.

DETAILED DESCRIPTION

Figure 1:
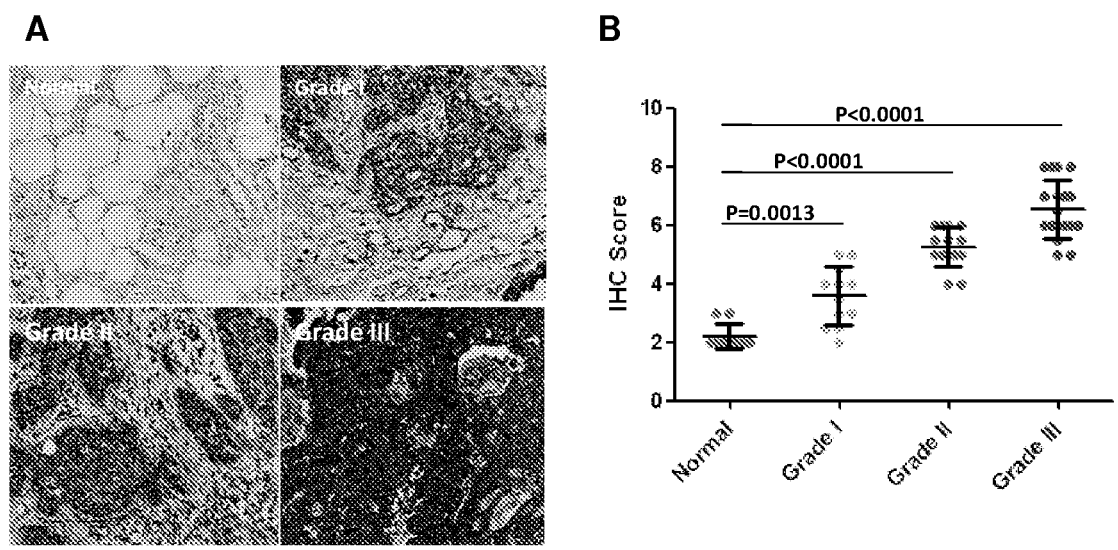
FIG. 1 shows (A) Immunohistochemistry of normal and tumorous breast tissue. The three tumor samples were graded by a certified pathologist. Monoclonal antibody to human UNC-45A was used detect the elevated levels. (B) Multiple samples were coded by blinded laboratory personnel for testing. UNC-45A protein elevation by histochemical stain consistently correlates with the metastatic grade. The bars are standard observations ($p<0.001$ for all pair comparisons).

The molecular interaction of UNC-45A with its protein partner Hsp90 and the target myosin motors, is exploited for molecular strategies for effective therapy of breast cancer.

In UNC-45A929, exons 1-4 have unique sequences that are not present in UNC-45A944. Therefore target sequences were selected from, for example, exon 2 to design shRNA for down regulating UNC-45A929. In UNC-45A944, about 45 nucleotides are unique when compared to UNC-45A929 and were therefore was selected as target sequences.

Antisense sequences generally loop with sense sequences to form hairpin. In an aspect, these oligonucleotides are ligated in "BLOCK-iT inducible RNAi" vector to transfect mammalian cells. This vector is tetracycline inducible to trigger the RNAi for down regulating UNC-45A929.

Knockdown experiments demonstrate that reduction of UNC-45A reduces the rates of cancer cell proliferation and migration whereas overexpression increases them. Data presented herein demonstrate that the elevation of UNC-45A in e.g., both breast tumor samples and breast cancer-derived cell lines is due to overexpression of only one of two alternative splice variants. This differential expression enables the use of UNC-45A as a specific biomarker and for highly specific RNA-based cancer therapeutics.

UNC-45A and its specific splice variant expression as correlating with established human breast carcinomas in terms of grade, metastasis, and prognosis are validated. Tissue block sections are analyzed by for example, immunohistochemistry and immunoblotting using specific monoclonal antibodies.

UNC-45A splice variants are validated as biomarkers using e.g., fresh serum and breast tissue samples from cancer patients. These samples are analyzed by for example, immunohistochemistry and immunoblotting using specific monoclonal antibodies and compared to standard histopathological methods.

RNAi using UNC-45A929 specific siRNA or shRNA or microRNA are developed as therapeutic agents against cancer. The effects of the RNAi agents on proliferation, migration and invasion in normal, non-metastatic, and metastatic cancer cell lines including breast cancer are tested.

RNA interference (RNAi) is the pathway by which short interfering RNA (siRNA) or short hairpin RNA (shRNA) are used to inactivate the expression of target genes. Synthetic small interfering (siRNAs) or expressed stem-loop RNAs (short-hairpin RNAs (shRNAs) or artificial microRNAs (miRNAs) have been delivered to cultured cells and organisms to inhibit or down regulate expression of a variety of genes. Expressed shRNA is transcribed in cells from a DNA template as a single-stranded RNA molecule (~50-100 bases). Complementary regions spaced by a small 'loop' cause the transcript to fold back on itself forming a 'short hairpin' in a manner analogous to natural microRNA. Recognition and processing by the RNAi machinery converts the shRNA into the corresponding siRNA. Some exemplary design strategies for creating shRNA templates can be found in McIntyre & Fanning (2006), BMC Biotechnology 6:1 (incorporated herein by reference).

The term short interfering nucleic acid, siRNA, short interfering RNA, short interfering nucleic acid molecule, short interfering oligonucleotide molecule, or chemically-modified short interfering nucleic acid molecule as used herein refers to any nucleic acid molecule capable of inhibiting or down regulating gene expression or viral replication, for example by mediating RNA interference "RNAi" or gene silencing in a sequence-specific manner.

Generally, shRNA or short hairpin RNA is an RNA molecule that contains a sense strand, antisense strand, and a short loop sequence between the sense and antisense fragments. Due to the complementarity of the sense and antisense fragments in their sequence, such RNA molecules tend to form hairpin-shaped double-stranded RNA (dsRNA). shRNA is cloned into a vector, allowing for expression by a pol III type promoter. The expressed shRNA is then exported into the cytoplasm where it is processed by dicer into siRNA which then get incorporated into the siRNA induced silencing complex (RISC). Small Interfering RNA (siRNA) are about 21-23 nucleotide double-stranded RNA molecules. Once incorporated into RISC they facilitate the cleavage and degradation of its recognized mRNA.

MicroRNAs (miRNA) are single-stranded RNA molecules of about 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

By RNA is meant a molecule comprising at least one ribonucleotide residue. By ribonucleotide" is meant a nucleotide with a hydroxyl group at the 2' position of a βD-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

A subject can be a mammal or mammalian cells, including a human or human cells.

The dsRNA molecules (e.g., siRNA and shRNA) can include naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative or dodecanoic acid bisdecylamide group. Alternatively, the modified nucleotide may be selected from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

In an aspect, polyethylene glycol (PEG) can be covalently attached to siRNA compounds disclosed herein. The attached PEG can be any molecular weight, preferably from about 2,000 to about 50,000 daltons (Da).

As used herein, "target sequence" refers to a contiguous portion of the nucleotide sequence of an mRNA molecule formed during the transcription of the UNC-45A929 splice variant, including mRNA that is a product of RNA processing of a primary transcription product. By "gene", or "target gene", is meant a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siRNA mediated RNA interference in modulating the activity of FRNA or ncRNA involved in functional or regulatory cellular processes.

The term complementary, when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions.

Oligonucleotide probes that specifically target UNC-45A 929 splice variant are disclosed herein. These probes range from about 10-100, 10-50, 100-750, 100-800 or 10-500 contiguous nucleotide residues of SEQ ID NO: 1 and may be specifically directed to nucleotide positions 1-835 of SEQ ID NO: 1.

Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For explanation of stringency of hybridization reactions, see Ausubel et al., Current Protocols in Molecular Biology, Wiley Interscience Publishers, (1995).

Stringent conditions or high stringency conditions, as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5.times.Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C. followed by a high-stringency wash consisting of 0.1×SSC containing EDTA at 55° C.

Moderately stringent conditions may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA that includes one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes disclosed herein.

Complementary sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms complementary, fully complementary and substantially complementary herein may be used with respect to the base matching between the sense strand and the antisense strand of a dsRNA, or between the antisense strand of a dsRNA and a target sequence, as will be understood from the context of their use.

As used herein, a polynucleotide which is substantially complementary to at least part of a messenger RNA (mRNA) refers to a polynucleotide which is substantially complementary to a contiguous portion of the mRNA of interest (e.g., encoding UNC-45A929). For example, a polynucleotide is complementary to at least a part of a UNC-45A929 mRNA if the sequence is substantially complementary to a non-interrupted portion of a mRNA encoding UNC-45A929.

The term double-stranded RNA or dsRNA, as used herein, refers to a ribonucleic acid molecule, or complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term sense strand, as used herein, generally refers to the strand of a dsRNA that includes a region that is substantially complementary to a region of the antisense strand.

The term asymmetric hairpin generally means a linear siRNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siRNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siRNA molecule can also include a 5'-terminal phosphate group that can be chemically modified. The loop portion of the asymmetric hairpin siRNA molecule can comprise nucleotides, non-nucleotides, linker molecules, or conjugate molecules as described herein.

The term asymmetric duplex generally refers to a siRNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siRNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Introducing into a cell, when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically.

In vitro introduction into a cell includes methods known in the art such as electroporation and lipofection.

The terms silence and inhibit the expression of, refer to the at least partial suppression of the expression of the UNC-45A929 splice variant or the 944 variant, as manifested by a reduction of the amount of mRNA transcribed from the UNC-45A929 splice variant which may be isolated from a first cell or group of cells in which the UNC-45A929 splice variant is transcribed and which has or have been treated such that the expression of the UNC-45A929 splice variant is inhibited, as compared to a second cell or group of cells substantially identical to the first cell or group of cells but which has or have not been so treated (control cells). The degree of inhibition can be greater than 50%, 60%, 75%, 80%, 90%, 95%, and 99%.

Alternatively, the degree of inhibition may be given in terms of a reduction of a parameter that is functionally linked to UNC-45A929 transcription, e.g. the amount of protein encoded by the UNC-45A929, or the number of cells displaying a certain phenotype, e.g apoptosis. In principle, UNC-45A929 silencing may be determined in any cell expressing the target, either constitutively or by genomic engineering, and by any appropriate assay.

For example, in certain instances, expression of the UNC-45A929 splice variant is suppressed by at least about 20%, 25%, 35%, or 50% by administration of the RNAi agents disclosed herein. In an aspect, the UNC-45A929 splice variant is suppressed by at least about 60%, 70%, or 80% by administration of the RNAi agents disclosed herein. In an aspect, the UNC-45A929 splice variant is suppressed by at least about 85%, 90%, or 95% by administration of the RNAi agents disclosed herein. In an aspect, the UNC-45A929 splice variant is suppressed by at least about 98%, 99% or more by administration of the RNAi agents disclosed herein.

The term "biomarker" as used in the present application refers generally to a DNA, RNA, protein, carbohydrate, or glycolipid-based molecular marker, the expression or presence of which in a subject's sample can be detected by standard methods (or methods disclosed herein) and is predictive or prognostic of the effective responsiveness or sensitivity of a mammalians subject with cancer. Expression of such a biomarker may be determined to be higher than that observed for a control sample. The terms "marker" and "biomarker" are used herein interchangeably. The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with a B-cell antagonist.

The terms "level of expression" or "expression level" in general are used interchangeably and generally refer to the amount of a polynucleotide or an amino acid product or protein in a biological sample. "Expression" generally refers to the process by which gene-encoded information is converted into the structures present and operating in the cell. Expression of a gene or a nucleic acid sequence may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. Expressed genes include those that are transcribed into a polynucleotide as mRNA and then translated into a protein, and also those that are transcribed into RNA but not translated into a protein (for example, transfer and ribosomal RNAs).

Methods for detecting any genetic biomarkers desired to be assessed in addition to the expression of UNC-45A929 include protocols that examine the presence and/or expression of a SNP, for example, in a sample. Tissue or cell samples from mammals can be conveniently assayed for, e.g., genetic-marker mRNAs or DNAs using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an aspect, a method for detecting a SNP mRNA in a biological sample comprises producing cDNA from the sample by reverse transcription using at least one primer; amplifying the cDNA so produced using a SNP polynucleotide as sense and antisense primers to amplify SNP cDNAs therein; and detecting the presence of the amplified SNP cDNA. In addition, such methods can include one or more steps that allow one to determine the levels of SNP mRNA in a biological sample (e.g., by simultaneously examining the levels a comparative control mRNA sequence of a "housekeeping" gene such as an actin family member). Optionally, the sequence of the amplified SNP cDNA can be determined.

In an aspect, genotyping of a polymorphism can be performed by RT-PCR technology, using the TAQMAN™ 5'-allele discrimination assay, a restriction fragment-length polymorphism PCR-based analysis, or any sequencing instrument.

Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of a SNP in a sample and as a means for detecting a cell expressing SNP-encoded proteins. As will be understood by the skilled artisan, a great many different primers and probes may be prepared based on known sequences and used effectively to amplify, clone, and/or determine the presence and/or levels of SNP mRNAs.

Other methods include protocols that examine or detect mRNAs in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment.

Diagnostic antibodies include monoclonal antibodies or antibody fragments that specifically bind to UNC-45A929 protein or a peptide thereof and antibodies or antibody fragments that specifically bind to UNC-45A944. The antibodies are used in a variety of samples including serum, tissue biopsies, isolated and purified tissue samples to perform antibody-based detection assays including western blotting; ELISA, sandwich ELISA and other known techniques. Antibodies that are able selectively bind to one or more epitopes present only on the 929 splice variant or the 944 splice variant are contemplated. For example, monoclonal antibodies directed specifically to bind to an epitope that include the additional 15 amino acids (3-17) of SEQ ID NO: 4 (UNC-45944 protein sequence) are contemplated.

The term treatment or therapeutics refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. A patient or subject may be a human, but can also be a non-human animal, e.g., vertebrate mammal. Treatment may generally refer to the reduction of one or more symptoms associated with cancer including extending the survival rate of an individual.

As used herein, the phrases therapeutically effective amount and prophylactically effective amount generally refer to an amount that provides a therapeutic benefit in the treatment or prevention of cancer or to minimize an overt symptom of the cancer. The specific amount that is therapeutically effective can be routinely determined by skilled artisans, and may vary depending on factors known in the art, such as, e.g. the type of cancer, the stage of the cancer and the patient's history and age and the administration of other anti-cancer agents. For example, if a given clinical treatment is considered effective when there is at least a 25% to 30% reduction in a measurable parameter associated with a disease or disorder, a therapeutically effective amount of a drug for the treatment of that disease or disorder is the amount necessary to effect at least a 25% reduction in that parameter.

As used herein, a pharmaceutical composition generally is intended to include a pharmacologically effective amount of an RNAi agent and a pharmaceutically acceptable carrier as this term is used in inhibiting or downregulating the expression of one or more UNC-45A splice variants.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a transformed cell is a cell into which a vector has been introduced from which a dsRNA molecule (e.g., shRNA) may be expressed to downregulate one or more splice variants of UNC-45A.

The reagents and compositions disclosed herein are used alone or as a component of a kit having at least one of the reagents necessary to carry out the in vitro or in vivo introduction of RNA to test samples and/or subjects. For example, some of the components of the kit include a siRNA molecule and a vehicle that facilitates introduction of the siRNA into cells of interest as described herein (e.g., using lipids, liposomes and non-liposomal formulations, viral vectors, nanoparticle-based delivery of nucleic acids and other methods of transfection known in the art). Such a kit can also include instructions to allow a user of the kit to practice the methods disclosed herein.

The term modulate or modulating generally means that the expression of the gene, or level of RNA molecule or the equivalent RNA molecules (e.g., splice variants) encoding one or more proteins or protein subunits, or activity of one or more proteins or protein subunits is up regulated or down regulated, such that the expression, level, or activity is greater than or less than that observed in the absence of the modulator. For example, the term modulate can mean inhibit or substantially reduced depending on the context in which the term is used.

The terms inhibit, down-regulate, or reduce, mean that the expression of the gene, or level of RNA molecules or equivalent RNA molecules (e.g., splice variants) encoding one or more proteins or protein subunits, or activity of one or more proteins or protein subunits, is reduced below that observed in the absence of the nucleic acid molecules (e.g., siRNA) disclosed herein. In an aspect, inhibition, down-regulation or reduction with an siRNA molecule is below that level observed in the presence of an inactive or attenuated molecule. In an aspect, inhibition, down-regulation, or reduction with siRNA molecules is below that level observed in the presence of, for example, an siRNA molecule with scrambled sequence or with mismatches. In an aspect, inhibition, down regulation, or reduction of gene expression is associated with post transcriptional silencing, such as RNAi mediated cleavage of a target nucleic acid molecule (e.g. RNA) or inhibition of translation. In an aspect, inhibition, down regulation, or reduction of gene expression is associated with pretranscriptional silencing.

In an aspect, the siRNA molecules are used to treat cancer or other proliferative diseases, disorders, and/or conditions in a subject or organism.

The terms cancer or proliferative disease generally mean any disease characterized by unregulated cell growth or replication as is known in the art; breast cancers; bone cancers such as Osteosarcoma, Chondrosarcomas, Ewing's sarcoma, fibrosarcomas, giant cell tumors, Adamantinomas, and Chordomas; brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration, corneal neovascularization, diabetic retinopathy, neovascular glaucoma, myopic degeneration and other proliferative diseases that can respond to the modulation of disease related gene (e.g., "UNC-45A929") expression in a cell or tissue, alone or in combination with other therapies.

The terms cell proliferative disorder and proliferative disorder generally refer to disorders that are associated with some degree of abnormal cell proliferation. In an aspect, the cell proliferative disorder is cancer.

The terms neoplasm or neoplastic cell refer to an abnormal tissue or cell that proliferates more rapidly than corresponding normal tissues or cells and continues to grow after removal of the stimulus that initiated the growth.

In an aspect, the disclosure provides double-stranded ribonucleic acid (dsRNA) molecules for inhibiting the expression of the UNC-45A929 splice variant (or the UNC-45A929 splice variant or both) in a cell or mammal, wherein the dsRNA comprises an antisense strand comprising a region of complementarity which is complementary to at least a part of an mRNA formed in the expression of the UNC-45A929 splice variant (or the UNC-45A929 splice variant or both), and wherein the region of complementarity is less than 30 nucleotides in length and wherein said dsRNA, upon contact with a cell expressing the UNC-45A929 splice variant (or the UNC-45A929 splice variant or both), inhibits the expression of said UNC-45A929 gene by at least 20%. The dsRNA comprises two RNA strands that are sufficiently complementary to hybridize to form a duplex structure. One strand of the dsRNA (the antisense strand) includes a region of complementarity that is substantially complementary, and preferably fully complementary, to a target sequence, derived from the sequence of an mRNA formed during the expression of the UNC-45A929 splice variant (or the UNC-45A929 splice variant or both), the other strand (the sense strand) comprises a region which is complementary to the antisense strand, such that the two strands hybridize and form a duplex structure when combined under suitable conditions. Preferably, the duplex structure is between 15 and 30, more preferably between 18 and 25, yet more preferably between 19 and 24, and most preferably between 21 and 23 base pairs in length. Similarly, the region of complementarity to the target sequence is between 15 and 30, more preferably between 18 and 25, yet more preferably between 19 and 24, and most preferably between 21 and 23 nucleotides in length. The dsRNA may further include one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc.

The dsRNA for the target molecules disclosed herein can contain one or more mismatches to the target sequence. In an aspect, the dsRNA contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the UNC-45A929 splice variant (or the UNC-45A929 splice variant or both), the dsRNA preferably does not contain any mismatch within the central 13 nucleotides. The methods described herein can be used to determine whether a dsRNA containing a mismatch to a target sequence is effective in inhibiting the expression of the UNC-45A929 splice variant. Consideration of the efficacy of dsRNAs with mismatches in inhibiting expression of the UNC-45A929 splice variant (or the UNC-45A929 splice variant or both) is relevant, if the particular region of complementarity in the UNC-45A gene is known to have polymorphic sequence variation within the population.

In an aspect, the dsRNA is chemically modified to enhance stability. The nucleic acids may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In an aspect, the 5'-end of the antisense strand and the 3'-end of the sense strand are chemically linked via a hexaethylene glycol linker. In an aspect, at least one nucleotide of the dsRNA includes a phosphorothioate or phosphorodithioate groups. The chemical bond at the ends of the dsRNA is formed e.g., by triple-helix bonds. In an aspect, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. The chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen.

In some aspects, a chemical bond may be formed by means of one or several bonding groups, wherein such bonding groups are preferably poly-(oxyphosphinicooxy-1,3-propandiol)- and/or polyethylene glycol chains. In some aspects, a chemical bond may also be formed by means of purine analogs introduced into the double-stranded structure instead of purines. In some aspects, a chemical bond may be formed by azabenzene units introduced into the double-stranded structure.

In an aspect, the nucleotides at one or both of the two single strands may be modified to prevent or inhibit the activation of cellular enzymes, such as, for example, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate. For example, at least one 2'-hydroxyl group of the nucleotides on a dsRNA is replaced by a chemical group, such as for example, by a 2'-amino or a 2'-methyl group. A nucleotide may also be modified to form a locked nucleotide. Such locked nucleotide contains a methylene bridge that connects the 2'-oxygen of ribose with the 4'-carbon of ribose.

In certain aspects, conjugating a ligand to a dsRNA enhances cellular absorption for in vivo applications. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches facilitate cell permeation of antisense oligonucleotides.

A siRNA or shRNA molecule can include any contiguous UNC-45A929 or 944 sequence (e.g., about 15 to about 25 or more, or about 15, 16, 17, 18, 19, 20, 21, 22, 23, 24, or 25 or more contiguous UNC-45A929 or 944 nucleotides).

In an aspect, a siRNA or shRNA molecule comprises an antisense strand having about 15 to about 30 (e.g., about 15, 16, 17, 18, 19, 20, 21, 22, 23, 24, 25, 26, 27, 28, 29, or 30)

nucleotides, wherein the antisense strand is complementary to a RNA sequence or a portion thereof encoding a UNC-45A929 protein, and wherein said siRNA or shRNA further comprises a sense strand having about 15 to about 30 (e.g., about 15, 16, 17, 18, 19, 20, 21, 22, 23, 24, 25, 26, 27, 28, 29, or 30) nucleotides, and wherein said sense strand and said antisense strand are distinct nucleotide sequences where at least about 15 nucleotides in each strand are complementary to the other strand.

In an aspect, a siRNA or shRNA molecule includes an antisense region having about 15 to about 30 (e.g., about 15, 16, 17, 18, 19, 20, 21, 22, 23, 24, 25, 26, 27, 28, 29, or 30) nucleotides, wherein the antisense region is complementary to a RNA sequence encoding a UNC-45A929 protein, and wherein said siRNA or shRNA further comprises a sense region having about 15 to about 30 (e.g., about 15, 16, 17, 18, 19, 20, 21, 22, 23, 24, 25, 26, 27, 28, 29, or 30) nucleotides, wherein said sense region and said antisense region are comprised in a linear molecule where the sense region comprises at least about 15 nucleotides that are complementary to the antisense region.

In an aspect, nucleic acid molecules that act as mediators of the RNA interference gene silencing response are double-stranded nucleic acid molecules. In an aspect, the siRNA or shRNA molecules consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In an aspect, siRNA or shRNA molecules include duplex nucleic acid molecules with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs. In an aspect, siRNA or shRNA molecules include duplex nucleic acid molecules with blunt ends, where both ends are blunt, or alternatively, where one of the ends is blunt.

In an aspect, one or more chemically-modified siRNA or shRNA constructs having specificity for UNC-45A929 or 944 expressing nucleic acid molecules, such as RNA encoding a UNC-45A929 protein. In an aspect, the disclosure includes a RNA based siRNA or shRNA molecule (e.g., a siRNA or shRNA comprising 2'-OH nucleotides) having specificity for UNC-45A929 expressing nucleic acid molecules that includes one or more chemical modifications described herein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siRNA or shRNA constructs, (e.g., RNA based siRNA or shRNA constructs), are shown to preserve RNAi activity in cells while at the same time, dramatically increasing the serum stability of these compounds.

In an aspect, a siRNA or shRNA molecule includes modified nucleotides while maintaining the ability to mediate RNAi. The modified nucleotides can be used to improve in vitro or in vivo characteristics such as stability, activity, and/or bioavailability. For example, a siRNA or shRNA includes modified nucleotides as a percentage of the total number of nucleotides present in the siRNA or shRNA molecule. As such, a siRNA or shRNA molecule generally includes about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siRNA or shRNA molecule will depend on the total number of nucleotides present in the siRNA or shRNA. If the siRNA or shRNA molecule is single stranded, the percent modification can be based upon the total number of nucleotides present in the single stranded siRNA molecules. Likewise, if the siRNA or shRNA molecule is double stranded, the percent modification can be based upon the total number of nucleotides present in the sense strand, antisense strand, or both the sense and antisense strands.

In an aspect, a double-stranded short interfering nucleic acid (siRNA or shRNA) molecule that down-regulates expression of a UNC-45A929/944 splice variant that includes an antisense region, wherein the antisense region includes a nucleotide sequence that is complementary to a nucleotide sequence of the UNC-45A929/944 splice variant or a portion thereof, and a sense region, wherein the sense region comprises a nucleotide sequence substantially similar to the nucleotide sequence of the UNC-45A929/944 splice variant or a portion thereof. In an aspect, the antisense region and the sense region independently comprise about 15 to about 30 (e.g. about 15, 16, 17, 18, 19, 20, 21, 22, 23, 24, 25, 26, 27, 28, 29, or 30) nucleotides, wherein the antisense region comprises about 15 to about 30 (e.g. about 15, 16, 17, 18, 19, 20, 21, 22, 23, 24, 25, 26, 27, 28, 29, or 30) nucleotides that are complementary to nucleotides of the sense region.

In an aspect, a double-stranded short interfering nucleic acid (siRNA or shRNA) molecule that down-regulates expression of a UNC-45A929/944 splice variant comprising a sense region and an antisense region, wherein the antisense region comprises a nucleotide sequence that is complementary to a nucleotide sequence of RNA encoded by the UNC-45A929/944 splice variant or a portion thereof and the sense region comprises a nucleotide sequence that is complementary to the antisense region.

In some aspects, the siRNA molecules are added directly, or can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers.

In another aspect, mammalian cells containing one or more siRNA or shRNA molecules disclosed herein are included. The one or more siRNA or shRNA molecules can independently be targeted to the same or different sites.

The nucleic acid molecules, individually, or in combination or in conjunction with other drugs, can be used to for preventing or treating cancer or proliferative diseases and conditions in a subject or organism.

For example, the siRNA or shRNA molecules can be administered to a subject or can be administered to other appropriate cells evident to those skilled in the art, individually or in combination with one or more drugs under conditions suitable for the treatment.

In an aspect, the siRNA or shRNA molecules can be used in combination with other known treatments to prevent or treat cancer, proliferative, or ocular diseases and conditions in a subject or organism. For example, the described molecules could be used in combination with one or more known compounds, treatments, or procedures to prevent or treat cancer in a subject or organism as are known in the art. Such available therapies include chemotherapy and radiation therapy. For chemotherapy, some of the known active ingredients include for example, doxorubicin, irinotecan, cyclophosphamide, chlorambucil, melphalan, methotrexate, cytarabine, fludarabine, 6-mercaptopurine, 5-fluorouracil, cisplatin, carboplatin, oxaliplatin, and a combination thereof. Some of the biological drugs include for example, antibody drugs to specific receptors such as for example, Gemtuzumab, cetuximab, and Bevicizumab.

In an aspect, the methods and compositions disclosed herein include an expression vector comprising a nucleic acid sequence encoding at least one siRNA or shRNA molecule to allow expression of the siRNA or shRNA molecule. For example, the vector can contain sequence(s) encoding both strands of a siRNA or shRNA molecule comprising a duplex. The vector can also contain sequence(s) encoding a single nucleic acid molecule that is self-complementary and thus forms a siRNA or shRNA molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500.

In an aspect, the methods and compositions disclosed herein include a mammalian cell, for example, a human cell, including an expression vector.

In another aspect a siRNA or shRNA molecule include one or more 5' and/or a 3'-cap structure, for example, on only the sense siRNA or shRNA strand, the antisense siRNA or shRNA strand, or both siRNA or shRNA strands.

Cap structure generally means chemical modifications that are included at either terminus of the oligonucleotides. These end modifications protect the nucleic acid molecule from exonuclease degradation, and may also help in delivery and/or localization within a cell. The cap may be present at the 5'-terminus (5'-cap) or at the 3'-terminal (3'-cap) or may be present on both the ends. Examples for the 5'-cap include, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

A siRNA or shRNA or miRNA molecule can be adapted for use to prevent or treat cancer. For example, a siRNA or shRNA or miRNA molecule includes a delivery vehicle, including liposomes, for administration to a subject, carriers and diluents and their salts, and/or can be present in pharmaceutically acceptable formulations. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins, biodegradable nanocapsules, and bioadhesive microspheres, or by proteinaceous vectors. In an aspect, the nucleic acid molecules can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In an aspect, a siRNA or shRNA or miRNA molecule is complexed with membrane disruptive agents. In an aspect, the membrane disruptive agent or agents and the siRNA molecule are also complexed with a cationic lipid or helper lipid molecule.

In an aspect, delivery systems include, for example, liposomes, permeation enhancers (e.g., fatty acids, fatty acid esters, fatty alcohols and amino acids), and hydrophilic polymers (e.g., polycarbophil and polyvinylpyrolidone). In one aspect, the pharmaceutically acceptable carrier is a liposome or a transdermal enhancer.

In an aspect, siRNA or shRNA or miRNA molecules are administered to a subject by systemic administration in a pharmaceutically acceptable composition or formulation. By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siRNA or shRNA or miRNA molecules to an accessible diseased tissue. A liposome formulation that can enhance the association of drug with the surface of cells, such as, lymphocytes and macrophages is also useful.

The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The term selectively inhibiting or selectively reducing generally means that the siRNA or shRNA sequences preferentially targets the 929 or the 944 splice variant and specifically downregulates the expression of the particular splice variant.

The term consisting essentially of refers to compositions that contain siRNA or shRNA or miRNA and may optionally contain any other components that do not materially affect the functional attributes of siRNA or shRNA or miRNA disclosed herein. When the term consists essentially of consisting essentially of is used in the context of sequences, it generally means that the recited sequences are required for the intended function and that other sequences may be included on either end that do not materially affect the intended function.

TABLE 1

UNC-45A 929 target and siRNA sequences

| Name | Sequence |
| --- | --- |
| UNC-45A 929 Target Sequence-1 | TGGCCGTCACTACCCTGGTTTCTTT SEQ ID NO: 5 |
| UNC-45A 929 Target Sequence-2 | GGACAGAGGTGGTAGTGAACT SEQ ID NO: 6 |
| UNC-45A 944 Target Sequence-1 | GGTCCAGGGACCCCGAGCCCCG SEQ ID NO: 7 |
| UNC-45A 944 Target Sequence-2 | GTGAGTGGTCCAGGGACCCC SEQ ID NO: 8 |
| UNC-45A 929 siRNA Sense Sequence | UGGCCGUCACUACCCUGGUUUCUUU SEQ ID NO: 9 |
| UNC-45A 929 siRNA Anti-Sense Sequence | AAAGAAACCAGGGUAGUGACGGCCA SEQ ID NO: 10 |

TABLE 1-continued

UNC-45A 929 target and siRNA sequences

| Name | Sequence |
|---|---|
| UNC-45A 944 siRNA Sense Sequence | GGUCCAGGGACCCCCGAGCCCCG SEQ ID NO: 11 |
| UNC-45A 944 siRNA Anti-Sense Sequence | CGGGGCUCGGGGGUCCCUGGACC SEQ ID NO: 12 |

TABLE 2

Exemplary siRNA target sequences for UNC-45A929 splice variant

| siRNA sequence targets |
|---|
| GTGGTAGTGAACTCTCATG SEQ ID NO: 13 |
| ACCGAAGTAACCCGCAATG SEQ ID NO: 14 |
| GAGTCACGGCCTAGAAAGA SEQ ID NO: 15 |
| AGGACAGAGGTGGTAGTGA SEQ ID NO: 16 |
| GACAGAGGTGGTAGTGAAC SEQ ID NO: 17 |
| GCTGAATTTGAGGCCCTGT SEQ ID NO: 18 |
| TGCTGACAGGCCTATCTGT SEQ ID NO: 19 |
| GTCTGATTCTCCAGAGGAA SEQ ID NO: 20 |
| CCTCTACAACCTACTGGTT SEQ ID NO: 21 |

EXAMPLES

The following examples are for illustrative purposes and are not intended to limit the scope of the disclosure.

Example 1

UNC-45A Splice Variants Levels in Breast Cancer Tissue

Immunohistochemistry was used to study the UNC-45A expression patterns in human breast cancer specimens. The UNC-45A mRNA and protein levels were quantified in several human breast cancer cell lines by qRT-PCR and Western Blots. In vitro cell lines were used to assess the effect of UNC-45A on cell growth, migration, and invasion.

Humans and other vertebrates produce two isoforms encoded in separate genes, UNC-45A expressed generally and UNC-45B expressed in heart and skeletal muscle. Humans and other mammals alternatively splice the UNC-45A mRNA to produce two spliceoform proteins, differing by a 15 amino acid-residue, proline-rich sequence near the N-terminus. In human breast cancer patient specimens, UNC-45A level is up-regulated dramatically in high grade groups. In metastatic breast cancer cell lines and other cancer cell lines including cervical and colon adenocarcinoma cell lines, the shorter spliceoform is over-expressed. Recombinant human UNC-45A pulls down myosins IIA, IIB and Hsp90 beta, which have been implicated in cell proliferation, migration, and critical processes in cancer metastasis.

Experiments are designed to validate that downregulation of UNC-45A splice variants prevent cancer progression both in vitro and in vivo. Interactions of UNC-45A, myosinII and Hsp90 are mechanistically linked to the metastatic behavior.

Figure 2:
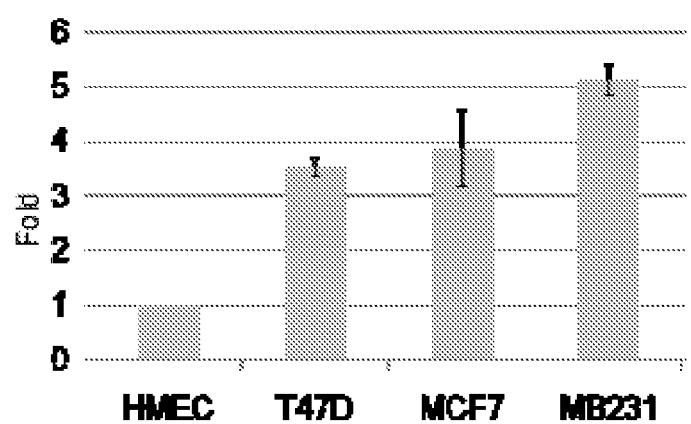
FIG. 2 shows UNC-45A levels in breast cancer cell lines. HMEC (normal breast) and T47D, MCF7, MB231 (breast cancer) cell lines were homogenized, and the protein lysates were separated on 8% SDS-PAGE and Western blotted with monoclonal antibody to human UNC-45A protein. The bars represent standard deviations.
Figure 3:
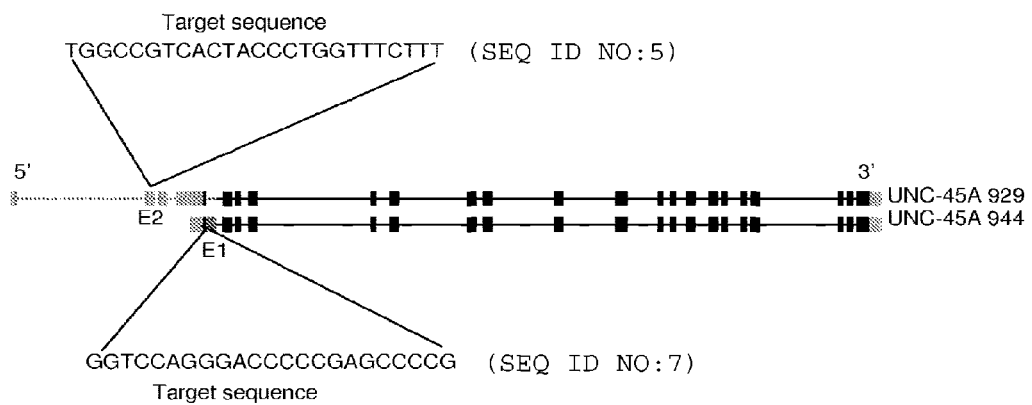
FIG. 3 shows siRNA oligos for knockdown of UNC-45A929 and 944.
Figure 4:
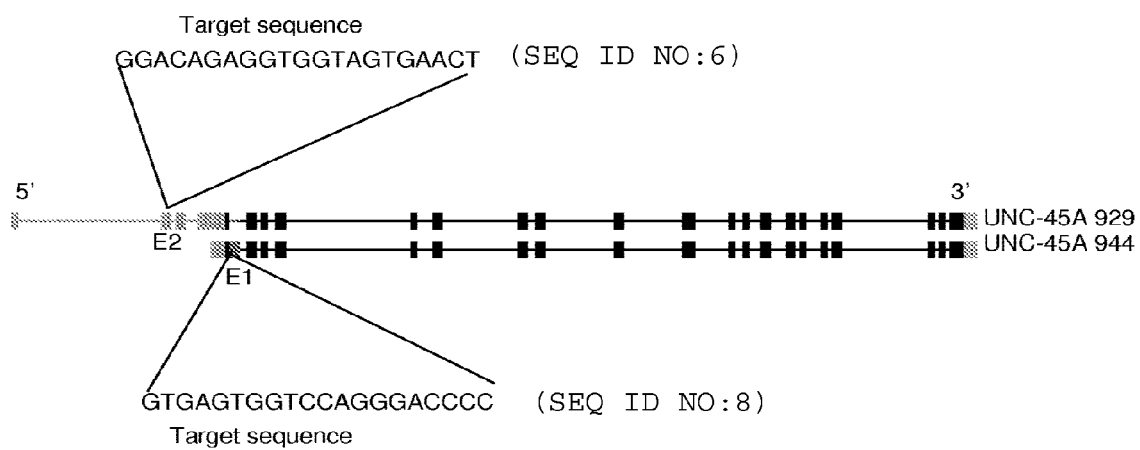
FIG. 4 illustrates shRNA target sequence for UNC-45A929 and UNC-45A944 splice variants.
Figure 5:
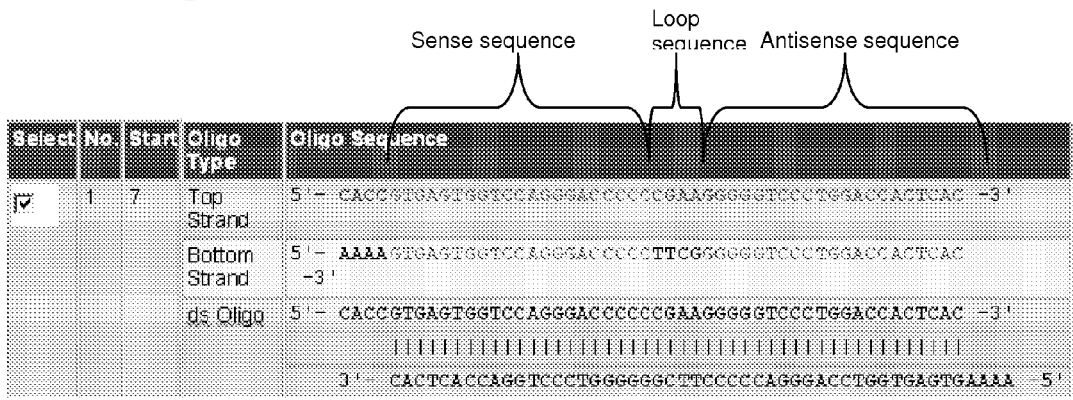
FIG. 5 illustrates shRNA design for UNC-45A944 (top strand is SEQ ID NO:24 and bottom strand is SEQ ID NO:25) and UNC-45A929 (top strand is SEQ ID NO:26 and bottom strand is SEQ ID NO:27) splice variants.
Figure 5:
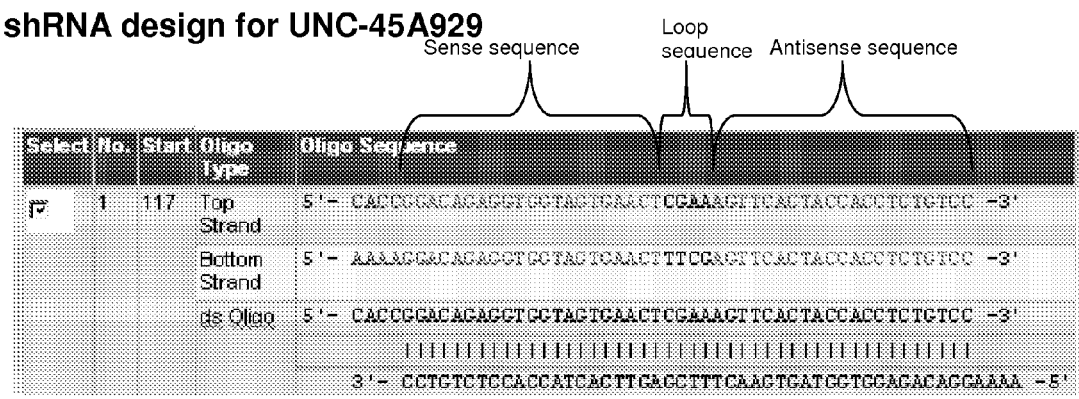

Human breast cancer tissues express higher levels of the UNC-45A gene products than normal breast tissues as shown in FIG. 1 illustrating immunohistochemistry of normal and tumorous breast tissue. UNC-45A levels in various breast cancer cell lines are also shown in FIG. 2.

The later stage tumors express higher levels of the UNC-45A gene products than the early stage tumors. Tumorigenic non-metastatic cell lines (MCF-7, T47D) express higher levels of UNC-45A proteins than non-tumorigenic cell line (HMEC). Tumorigenic metastatic cell line (MDA-MB-231) also expresses higher UNC-45A levels than non-tumorigenic cell lines.

These results show that UNC-45A levels are elevated in breast cancer and that UNC-45A929 splice variant is expressed to a higher level in metastatic cancers.

Example 2

UNC-45A Splice Variants Phosphorylation Status and Degradation

The extra 15 amino acids (VSGPGTPEPRPATPG) of the 944 variant confer about 5-fold higher degradation rate for the 944 variant than the 929 variant. In addition, the 15 additional amino acids present only in the 944 variant contain the only phosphorylatable site, T15 (as in the entire protein SEQ ID NO: 4) in the UNC-45A protein. Therefore, the 944 variant is regulated but degraded more rapidly whereas the 929 builds up to higher levels in several cancers and is not regulated by phosphorylation. The 929 splice variant does not contain the phosphorylatable T15.

The increased degradation of the 944 splice variant is used as both a diagnostic tool and a therapeutic target for the detection and treatment of cancers.

Sequence Information:

UNC-45A Human homolog A encoding the splice variants (944 and 929) splice is accessible at SwissProt by Acc. No. Q9H3U1. *Homo sapiens* (human) UNC-45A gene sequence is also accessible at NCBI by using a unigene identifier Uni-Gene Hs.389461.

UNC-45A929 Splice Variant Sequences

Highlighted by underlining (1-835) is a unique sequence present only in the UNC-45A929 splice variant and is absent in UNC-45A944. This is a non-coding sequence at 5' region. The nucleic acid sequence of UNC-45A929 splice variant (SEQ ID NO: 1) is shown herein.

```
 1 ACTTAACAACCGAAGTAACCCGCAATGCGGAAGGGCGAGGGGATTGCGAGTCACCGAGTT(SEQ ID NO: 1)
   ............................................................(SEQ ID NO: 3)

61 TCCCGCGCGGCTTGAGTCACGGCCTAGAAAGAGAGATGTTGGGGTTCCCAGGACCAGGAC
   ............................................................
```

-continued

```
 121 AGAGGTGGTAGTGAACTCTCATGGGCATCCAGAGAAGGTCAGGCCCCTTGCTGACAGGCC
     ............................................................

181 TATCTGTGGGCTACTGCTGCTCTTCAGCTGGGTGACCCTTGTCCAGCCAACCTCTCTCT
     ............................................................

241 CAGCTCTGGTCCACCACCCTCACTTGTGCCAGACCACCCGGGATGTCCATGGCCGTCACT
     ............................................................

301 ACCCTGGTTTCTTTTGCCCTCGTCTGTCTGATTCTCCAGAGGAAGCCTACTGCTGCCACC
     ............................................................

361 TGCAGGCTGCAGGGGGCTCCTGCTGCACCCGGGCTGAATTTGAGGCCCTGTACCAAGTCA
     ............................................................

421 ATCTGTCCGCTCTTCCGCCCCCGCCCATCCTCAGGGGCCCAGGCCCGCTCCTAGTGCTGG
     ............................................................

481 GCCTCTACAACCTACTGGTTGTGACCCTGATGACCGTAGACCTCGTGCACTTCTGCTGCG
     ............................................................

541 GTCGGGGCCGGAGTCTGGGCTGGAGCCACCGCAGGCCTCCCTCTGGGTCCTCCGCCGCGA
     ............................................................

601 GCTCCCTGCAGGTCTCTGCGGGGACAGCTTAGGTGCGCCCGGAGCTTGCCTGCACCTGCG
     ............................................................

661 ATCCAGAGCCAAGCGCCCCGCCCCTGCCCGGGCGCGCTCCCTCCTTAGCCCTGCCCCTCT
     ............................................................

721 CTGACCCCACCTCCGACGCAAGAGTGGGGCGGGGCAGCTGCCGGTGGCGTCCCGAACCCA
     ............................................................

781 GACTCGCCCCGCCCCAGAGACTGCGCCTGCGCGGGCACGAGACAACCTCTCCGCGATGAC
     .........................................................-M--T

841 TGCCAGCTCAGTGGAGCAGCTGCGGAAGGAGGGCAATGAGCTGTTCAAATGTGGAGACTA
   2 --A--S--S--V--E--Q--L--R--K--E--G--N--E--L--F--K--C--G--D--Y

901 CGGGGGCGCCCTGGCGGCCTACACTCAGGCCCTGGGTCTGGACGCGACGCCCCAGGACCA
  22 --G--G--A--L--A--A--Y--T--Q--A--L--G--L--D--A--T--P--Q--D--Q

961 GGCCGTTCTGCACCGGAACCGGGCCGCCTGCCACCTCAAGCTGGAAGATTACGACAAAGC
  42 --A--V--L--H--R--N--R--A--A--C--H--L--K--L--E--D--Y--D--K--A

1021 AGAAACAGAGGCATCCAAAGCCATTGAAAAGGATGGTGGGGATGTCAAAGCACTCTACCG
  62 --E--T--E--A--S--K--A--I--E--K--D--G--G--D--V--K--A--L--Y--R

1081 GCGGAGCCAAGCCCTAGAGAAGCTGGGCCGCCTGGACCAGGCTGTCCTTGACCTGCAGAG
  82 --R--S--Q--A--L--E--K--L--G--R--L--D--Q--A--V--L--D--L--Q--R

1141 ATGTGTGAGCTTGGAGCCCAAGAACAAAGTTTTCCAGGAGGCCTTGCGGAACATCGGGGG
 102 --C--V--S--L--E--P--K--N--K--V--F--Q--E--A--L--R--N--I--G--G

1201 CCAGATTCAGGAGAAGGTGCGATACATGTCCTCGACGGATGCCAAAGTGGAACAGATGTT
 122 --Q--I--Q--E--K--V--R--Y--M--S--S--T--D--A--K--V--E--Q--M--F

1261 TCAGATACTGTTGGACCCAGAAGAGAAGGGCACTGAGAAAAAGCAAAAGGCTTCTCAGAA
 142 --Q--I--L--L--D--P--E--E--K--G--T--E--K--K--Q--K--A--S--Q--N

1321 CCTGGTGGTGCTGGCCAGGGAGGATGCTGGAGCGGAGAAGATCTTCCGGAGTAATGGGGT
 162 --L--V--V--L--A--R--E--D--A--G--A--E--K--I--F--R--S--N--G--V

1381 TCAGCTCTTGCAACGTTTACTGGACATGGGAGAGACTGACCTCATGCTGGCGGCTCTGCG
 182 --Q--L--L--Q--R--L--L--D--M--G--E--T--D--L--M--L--A--A--L--R

1441 TACGCTGGTTGGCATTTGCTCTGAGCATCAGTCACGGACAGTGGCAACCCTGAGCATACT
 202 --T--L--V--G--I--C--S--E--H--Q--S--R--T--V--A--T--L--S--I--L

1501 GGGAACTCGGCGAGTAGTCTCCATCCTGGGCGTGAAAGCCAGGCTGTGTCCCTGGCTGC
 222 --G--T--R--R--V--V--S--I--L--G--V--E--S--Q--A--V--S--L--A--A

1561 CTGCCACCTGCTGCAGGTTATGTTTGATGCCCTCAAGGAAGGTGTCAAAAAAGGCTTCCG
 242 --C--H--L--L--Q--V--M--F--D--A--L--K--E--G--V--K--K--G--F--R

1621 AGGCAAAGAAGGTGCCATCATTGTGGATCCTGCCCGGGAGCTGAAGGTCCTCATCAGTAA
 262 --G--K--E--G--A--I--I--V--D--P--A--R--E--L--K--V--L--I--S--N

1681 CCTCTTAGATCTGCTGACAGAGGTGGGGGTCTCTGGCCAAGGCCGAGACAATGCCCTGAC
 282 --L--L--D--L--L--T--E--V--G--V--S--G--Q--G--R--D--N--A--L--T
```

```
-continued

1741 CCTCCTGATTAAAGCGGTGCCCCGGAAGTCTCTCAAGGACCCCAACAACAGCCTCACCCT
 302 --L--L--I--K--A--V--P--R--K--S--L--K--D--P--N--N--S--L--T--L

1801 CTGGGTCATCGACCAAGGTCTGAAAAAGATTTTGGAAGTGGGGGGCTCTCTACAGGACCC
 322 --W--V--I--D--Q--G--L--K--K--I--L--E--V--G--G--S--L--Q--D--P

1861 TCCTGGGGAGCTCGCAGTGACCGCAAACAGCCGCATGAGCGCCTCTATTCTCCTCAGCAA
 342 --P--G--E--L--A--V--T--A--N--S--R--M--S--A--S--I--L--L--S--K

1921 GCTCTTTGATGACCTCAAGTGTGATGCGGAGAGGGAGAATTTCCACAGACTTTGTGAAAA
 362 --L--F--D--D--L--K--C--D--A--E--R--E--N--F--H--R--L--C--E--N

1981 CTACATCAAGAGCTGGTTTGAGGGCCAAGGGCTGGCCGGGAAGCTACGGGCCATCCAGAC
 382 --Y--I--K--S--W--F--E--G--Q--G--L--A--G--K--L--R--A--I--Q--T

2041 GGTGTCCTGCCTCCTGCAGGGCCCATGTGACGCTGGCAACCGGGCCTTGGAGCTGAGCGG
 402 --V--S--C--L--L--Q--G--P--C--D--A--G--N--R--A--L--E--L--S--G

2101 TGTCATGGAGAGTGTGATTGCTCTGTGTGCCTCTGAGCAGGAGGAGGAGCAGCTGGTGGC
 422 --V--M--E--S--V--I--A--L--C--A--S--E--Q--E--E--E--Q--L--V--A

2161 CGTGGAGGCTCTGATCCATGCAGCCGGCAAGGCTAAGCGGGCCTCATTCATCACTGCCAA
 442 --V--E--A--L--I--H--A--A--G--K--A--K--R--A--S--F--I--T--A--N

2221 TGGTGTCTCGCTGCTGAAGGACCTATATAAGTGCAGCGAGAAGGACAGCATCCGCATCCG
 462 --G--V--S--L--L--K--D--L--Y--K--C--S--E--K--D--S--I--R--I--R

2281 GGCGCTAGTGGGACTCTGTAAGCTCGGTTCGGCTGGAGGGACTGACTTCAGCATGAAGCA
 482 --A--L--V--G--L--C--K--L--G--S--A--G--G--T--D--F--S--M--K--Q

2341 GTTTGCTGAAGGCTCCACTCTCAAACTGGCTAAGCAGTGTCGAAAGTGGCTGTGCAATGA
 502 --F--A--E--G--S--T--L--K--L--A--K--Q--C--R--K--W--L--C--N--D

2401 CCAGATCGACGCAGGCACTCGGCGCTGGGCAGTGGAGGGCCTGGCTTACCTGACCTTTGA
 522 --Q--I--D--A--G--T--R--R--W--A--V--E--G--L--A--Y--L--T--F--D

2461 TGCCGACGTGAAGGAAGAGTTTGTGGAGGATGCGGCTGCTCTGAAAGCTCTGTTCCAGCT
 542 --A--D--V--K--E--E--F--V--E--D--A--A--A--L--K--A--L--F--Q--L

2521 CAGCAGGTTGGAGGAGAGGTCAGTGCTCTTTGCGGTGGCCTCAGCGCTGGTGAACTGCAC
 562 --S--R--L--E--E--R--S--V--L--F--A--V--A--S--A--L--V--N--C--T

2581 CAACAGCTATGACTACGAGGAGCCCGACCCCAAGATGGTGGAGCTGGCCAAGTATGCCAA
 582 --N--S--Y--D--Y--E--E--P--D--P--K--M--V--E--L--A--K--Y--A--K

2641 GCAGCATGTGCCCGAGCAGCACCCCAAGGACAAGCCAAGCTTCGTGCGGGCTCGGGTGAA
 602 --Q--H--V--P--E--Q--H--P--K--D--K--P--S--F--V--R--A--R--V--K

2701 GAAGCTGCTGGCAGCGGGTGTGGTGTCGGCCATGGTGTGCATGGTGAAGACGGAGAGCCC
 622 --K--L--L--A--A--G--V--V--S--A--M--V--C--M--V--K--T--E--S--P

2761 TGTGCTGACCAGTTCCTGCAGAGAGCTGCTCTCCAGGGTCTTCTTGGCTTTAGTGGAAGA
 642 --V--L--T--S--S--C--R--E--L--L--S--R--V--F--L--A--L--V--E--E

2821 GGTAGAGGACCGAGGCACTGTGGTTGCCCAGGGAGGCGGCAGGGCGCTGATCCCGCTGGC
 662 --V--E--D--R--G--T--V--V--A--Q--G--G--R--A--L--I--P--L--A

2881 CCTGGAAGGCACGGACGTGGGGCAGACAAAGGCAGCCCAGGCCCTTGCCAAGCTCACCAT
 682 --L--E--G--T--D--V--G--Q--T--K--A--A--Q--A--L--A--K--L--T--I

2941 CACCTCCAACCCGGAGATGACCTTCCCTGGCGAGCGGATCTATGAGGTGGTCCGGCCCCT
 702 --T--S--N--P--E--M--T--F--P--G--E--R--I--Y--E--V--V--R--P--L

3001 CGTCTCCCTGTTGCACCTCAACTGCTCAGGCCTGCAGAACTTCGAGGCGCTCATGGCCCT
 722 --V--S--L--L--H--L--N--C--S--G--L--Q--N--F--E--A--L--M--A--L

3061 AACAAACCTGGCTGGGATCAGCGAGAGGCTCCGGCAGAAGATCCTGAAGGAGAAGGCTGT
 742 --T--N--L--A--G--I--S--E--R--L--R--Q--K--I--L--K--E--K--A--V

3121 GCCCATGATAGAAGGCTACATGTTTGAGGAGCATGAGATGATCCGCCGGGCAGCCACGGA
 762 --P--M--I--E--G--Y--M--F--E--E--H--E--M--I--R--R--A--A--T--E

3181 GTGCATGTGTAACTTGGCCATGAGCAAGGAGGTGCAGGACCTCTTCGAAGCCCAGGGCAA
 782 --C--M--C--N--L--A--M--S--K--E--V--Q--D--L--F--E--A--Q--G--N
                                                              Y

3241 TGACCGACTGAAGCTGCTGGTGCTGTACAGTGGAGAGGATGATGAGCTGCTACAGCGGGC
 802 --D--R--L--K--L--L--V--L--Y--S--G--E--D--D--E--L--L--Q--R--A
```

```
-continued
3301 AGCTGCCGGGGGCTTGGCCATGCTTACCTCCATGCGGCCCACGCTCTGCAGCCGCATTCC
 822 --A--A--G--G--L--A--M--L--T--S--M--R--P--T--L--C--S--R--I--P 3361 CCAAGTGACCACACACTGGCTGGAGATCCTGCAGGCCCTGCTTCTGAGCTCCAACCAGGA
 842 --Q--V--T--T--H--W--L--E--I--L--Q--A--L--L--L--S--S--N--Q--E 3421 GCTGCAGCACCGGGGTGCTGTGGTGGTGCTGAACATGGTGGAGGCCTCGAGGGAGATTGC
 862 --L--Q--H--R--G--A--V--V--V--L--N--M--V--E--A--S--R--E--I--A 3481 CAGCACCCTGATGGAGAGTGAGATGATGGAGATCTTGTCAGTGCTAGCTAAGGGTGACCA
 882 --S--T--L--M--E--S--E--M--M--E--I--L--S--V--L--A--K--G--D--H 3541 CAGCCCTGTCACAAGGGCTGCTGCAGCCTGCCTGGACAAAGCAGTGGAATATGGGCTTAT
 902 --S--P--V--T--R--A--A--A--A--C--L--D--K--A--V--E--Y--G--L--I

3601 CCAACCCAACCAAGATGGAGAGTGA
 922 --Q--P--N--Q--D--G--E--*-
```

UNC-45A944 Splice Variant

Highlighted by underlining (7-50) is a unique nucleic sequence present only in UNC-45A944 splice variant and is absent in UNC-45A929. This coding sequence adds 15 unique amino acids (3-17) in the amino acid sequence of UNC-45A944 shown herein. The nucleic acid sequence of UNC-45A944 splice variant (SEQ ID NO: 2) is shown herein.

```
   1 ATGACTGTGAGTGGTCCAGGGACCCCCGAGCCCCGGCCGGCCACCCCCGGGGCCAGCTCA (SEQ ID NO: 2)
   1 -M--T--V--S--G--P--G--T--P--E--P--R--P--A--T--P--G--A--S--S- (SEQ ID NO: 4)

61 GTGGAGCAGCTGCGGAAGGAGGGCAATGAGCTGTTCAAATGTGGAGACTACGGGGGCGCC
  21 -V--E--Q--L--R--K--E--G--N--E--L--F--K--C--G--D--Y--G--G--A-

121 CTGGCGGCCTACACTCAGGCCCTGGGTCTGGACGCGACGCCCCAGGACCAGGCCGTTCTG
  41 -L--A--A--Y--T--Q--A--L--G--L--D--A--T--P--Q--D--Q--A--V--L-

181 CACCGGAACCGGGCCGCCTGCCACCTCAAGCTGGAAGATTACGACAAAGCAGAAACAGAG
  61 -H--R--N--R--A--A--C--H--L--K--L--E--D--Y--D--K--A--E--T--E-

241 GCATCCAAAGCCATTGAAAAGGATGGTGGGGATGTCAAAGCACTCTACCGGCGGAGCCAA
  81 -A--S--K--A--I--E--K--D--G--G--D--V--K--A--L--Y--R--R--S--Q-

301 GCCCTAGAGAAGCTGGGCCGCCTGGACCAGGCTGTCCTTGACCTGCAGAGATGTGTGAGC
 101 -A--L--E--K--L--G--R--L--D--Q--A--V--L--D--L--Q--R--C--V--S-

361 TTGGAGCCCAAGAACAAAGTTTTCCAGGAGGCCTTGCGGAACATCGGGGGCCAGATTCAG
 121 -L--E--P--K--N--K--V--F--Q--E--A--L--R--N--I--G--G--Q--I--Q-

421 GAGAAGGTGCGATACATGTCCTCGACGGATGCCAAAGTGGAACAGATGTTTCAGATACTG
 141 -E--K--V--R--Y--M--S--S--T--D--A--K--V--E--Q--M--F--Q--I--L-

481 TTGGACCCAGAAGAGAAGGGCACTGAGAAAAAGCAAAAGGCTTCTCAGAACCTGGTGGTG
 161 -L--D--P--E--E--K--G--T--E--K--K--Q--K--A--S--Q--N--L--V--V-

541 CTGGCCAGGGAGGATGCTGGAGCGGAGAAGATCTTCCGGAGTAATGGGGTTCAGCTCTTG
 181 -L--A--R--E--D--A--G--A--E--K--I--F--R--S--N--G--V--Q--L--L-

601 CAACGTTTACTGACATGGGAGAGACTGACCTCATGCTGGCGGCTCTGCGTACGCTGGTT
 201 -Q--R--L--L--D--M--G--E--T--D--L--M--L--A--A--L--R--T--L--V-

661 GGCATTTGCTCTGAGCATCAGTCACGGACAGTGGCAACCCTGAGCATACTGGGAACTCGG
 221 -G--I--C--S--E--H--Q--S--R--T--V--A--T--L--S--I--L--G--T--R-

721 CGAGTAGTCTCCATCCTGGGCGTGGAAAGCCAGGCTGTGTCCCTGGCTGCCTGCCACCTG
 241 -R--V--V--S--I--L--G--V--E--S--Q--A--V--S--L--A--A--C--H--L-

781 CTGCAGGTTATGTTTGATGCCCTCAAGGAAGGTGTCAAAAAAGGCTTCCGAGGCAAAGAA
 261 -L--Q--V--M--F--D--A--L--K--E--G--V--K--K--G--F--R--G--K--E-

841 GGTGCCATCATTGTGGATCCTGCCCGGGAGCTGAAGGTCCTCATCAGTAACCTCTTAGAT
 281 -G--A--I--I--V--D--P--A--R--E--L--K--V--L--I--S--N--L--L--D-

901 CTGCTGACAGAGGTGGGGGTCTCTGGCCAAGGCCGAGACAATGCCCTGACCCTCCTGATT
 301 -L--L--T--E--V--G--V--S--G--Q--G--R--D--N--A--L--T--L--L--I-

961 AAAGCGGTGCCCCGGAAGTCTCTCAAGGACCCCAACAACAGCCTCACCCTCTGGGTCATC
 321 -K--A--V--P--R--K--S--L--K--D--P--N--N--S--L--T--L--W--V--I-

1021 GACCAAGGTCTGAAAAAGATTTTGGAAGTGGGGGGCTCTCTACAGGACCCTCCTGGGGAG
 341 -D--Q--G--L--K--K--I--L--E--V--G--G--S--L--Q--D--P--P--G--E-
```

```
1081 CTCGCAGTGACCGCAAACAGCCGCATGAGCGCCTCTATTCTCCTCAGCAAGCTCTTTGAT
 361 -L--A--V--T--A--N--S--R--M--S--A--S--I--L--L--S--K--L--F--D-

1141 GACCTCAAGTGTGATGCGGAGAGGGAGAATTTCCACAGACTTTGTGAAAACTACATCAAG
 381 -D--L--K--C--D--A--E--R--E--N--F--H--R--L--C--E--N--Y--I--K-

1201 AGCTGGTTTGAGGGCCAAGGGCTGGCCGGGAAGCTACGGGCCATCCAGACGGTGTCCTGC
 401 -S--W--F--E--G--Q--G--L--A--G--K--L--R--A--I--Q--T--V--S--C-

1261 CTCCTGCAGGGCCC⁕TGTGACGCTGGCAACCGGGCCTTGGAGCTGAGCGGTGTCATGGAG
 421 -L--L--Q--G--P--C--D--A--G--N--R--A--L--E--L--S--G--V--M--E-

1321 AGTGTGATTGCTCTGTGTGCCTCTGAGCAGGAGGAGGAGCAGCTGGTGGCCGTGGAGGCT
 441 -S--V--I--A--L--C--A--S--E--Q--E--E--E--Q--L--V--A--V--E--A-

1381 CTGATCCATGCAGCCGGCAAGGCTAAGCGGGCCTCATTCATCACTGCCAATGGTGTCTCG
 461 -L--I--H--A--A--G--K--A--K--R--A--S--F--I--T--A--N--G--V--S-

1441 CTGCTGAAGGACCTATATAAGTGCAGCGAGAAGGACAGCATCCGCATCCGGGCGCTAGTG
 481 -L--L--K--D--L--Y--K--C--S--E--K--D--S--I--R--I--R--A--L--V-

1501 GGACTCTGTAAGCTCGGTTCGGCTGGAGGGACTGACTTCAGCATGAAGCAGTTTGCTGAA
 501 -G--L--C--K--L--G--S--A--G--G--T--D--F--S--M--K--Q--F--A--E-

1561 GGCTCCACTCTCAAACTGGCTAAGCAGTGTCGAAAGTGGCTGTGCAATGACCAGATCGAC
 521 -G--S--T--L--K--L--A--K--Q--C--R--K--W--L--C--N--D--Q--I--D-

1621 GCAGGCACTCGGCGCTGGGCAGTGGAGGGCCTGGCTTACCTGACCTTTGATGCCGACGTG
 541 -A--G--T--R--R--W--A--V--E--G--L--A--Y--L--T--F--D--A--D--V-

1681 AAGGAAGAGTTTGTGGAGGATGCGGCTGCTCTGAAAGCTCTGTTCCAGCTCAGCAGGTTG
 561 -K--E--E--F--V--E--D--A--A--A--L--K--A--L--F--Q--L--S--R--L-

1741 GAGGAGAGGTCAGTGCTCTTTGCGGTGGCCTCAGCGCTGGTGAACTGCCCAACAGCTAT
 581 -E--E--R--S--V--L--F--A--V--A--S--A--L--V--N--C--T--N--S--Y-

1801 GACTACGAGGAGCCCGACCCCAAGATGGTGGAGCTGGCCAAGTATGCCAAGCAGCATGTG
 601 -D--Y--E--E--P--D--P--K--M--V--E--L--A--K--Y--A--K--Q--H--V-

1861 CCCGAGCAGCACCCCAAGGACAAGCCAAGCTTCGTGCGGGCTCGGGTGAAGAAGCTGCTG
 621 -P--E--Q--H--P--K--D--K--P--S--F--V--R--A--R--V--K--K--L--L-

1921 GCAGCGGGTGTGGTGTCGGCCATGGTGTGCATGGTGAAGACGGAGAGCCCTGTGCTGACC
 641 -A--A--G--V--V--S--A--M--V--C--M--V--K--T--E--S--P--V--L--T-

1981 AGTTCCTGCAGAGAGCTGCTCTCCAGGGTCTTCTTGGCTTTAGTGGAAGAGGTAGAGGAC
 661 -S--S--C--R--E--L--L--S--R--V--F--L--A--L--V--E--E--V--E--D-

2041 CGAGGCACTGTGGTTGCCCAGGGAGGCGGCAGGGCGCTGATCCCGCTGGCCCTGGAAGGC
 681 -R--G--T--V--V--A--Q--G--G--G--R--A--L--I--P--L--A--L--E--G-

2101 ACGGACGTGGGGCAGACAAAGGCAGCCCAGGCCCTTGCCAAGCTCACCATCACCTCCAAC
 701 -T--D--V--G--Q--T--K--A--A--Q--A--L--A--K--L--T--I--T--S--N-

2161 CCGGAGATGACCTTCCCTGGCGAGCGGATCTATGAGGTGGTCCGGCCCCTCGTCTCCCTG
 721 -P--E--M--T--F--P--G--E--R--I--Y--E--V--V--R--P--L--V--S--L-

2221 TTGCACCTCAACTGCTCAGGCCTGCAGAACTTCGAGGCGCTCATGGCCCTAACAAACCTG
 741 -L--H--L--N--C--S--G--L--Q--N--F--E--A--L--M--A--L--T--N--L-

2281 GCTGGGATCAGCGAGAGGCTCCGGCAGAAGATCCTGAAGGAGAAGGCTGTGCCCATGATA
 761 -A--G--I--S--E--R--L--R--Q--K--I--L--K--E--K--A--V--P--M--I-

2341 GAAGGCTACATGTTTGAGGAGCATGAGATGATCCGCCGGGCAGCCACGGAGTGCATGTGT
 781 -E--G--Y--M--F--E--E--H--E--M--I--R--R--A--A--T--E--C--M--C-

2401 AACTTGGCCATGAGCAAGGAGGTGCAGGACCTCTTCGAAGCCCAGGGCAATGACCGACTG
 801 -N--L--A--M--S--K--E--V--Q--D--L--F--E--A--Q--G--N--D--R--L-

2461 AAGCTGCTGGTGCTGTACAGTGGAGAGGATGATGAGCTGCTACAGCGGGCAGCTGCCGGG
 821 -K--L--L--V--L--Y--S--G--E--D--D--E--L--L--Q-R--A--A--A--G-

2521 GGCTTGGCCATGCTTACCTCCATGCGGCCCACGCTCTGCAGCCGCATTCCCCAAGTGACC
 841 -G--L--A--M--L--T--S--M--R--P--T--L--C--S--R--I--P--Q--V--T-

2581 ACACACTGGCTGGAGATCCTGCAGGCCCTGCTTCTGAGCTCCAACCAGGAGCTGCAGCAC
 861 -T--H--W--L--E--I--L--Q--A--L--L--L--S--S--N--Q--E--L--Q--H-

2641 CGGGGTGCTGTGGTGGTGCTGAACATGGTGGAGGCCTCGAGGGAGATTGCCAGCACCCTG
 881 -R--G--A--V--V--V--L--N--M--V--E--A--S--R--E--I--A--S--T--L-
```

-continued

```
2701 ATGGAGAGTGAGATGATGGAGATCTTGTCAGTGCTAGCTAAGGGTGACCACAGCCCTGTC
 901 -M--E--S--E--M--M--E--I--L--S--V--L--A--K--G--D--H--S--P--V-

2761 ACAAGGGCTGCTGCAGCCTGCCTGGACAAAGCAGTGGAATATGGGCTTATCCAACCCAAC
 921 -T--R--A--A--A--A--C--L--D--K--A--V--E--Y--G--L--I--Q--P--N-

2821 CAAGATGGAGAGTGA
 941 -Q--D--G--E--*-
```

SEQUENCE LISTING

```
<160> NUMBER OF SEQ ID NOS: 27

<210> SEQ ID NO 1
<211> LENGTH: 3625
<212> TYPE: DNA
<213> ORGANISM: Homo sapiens
<220> FEATURE:
<221> NAME/KEY: CDS
<222> LOCATION: (836)..(3622)

<400> SEQUENCE: 1
acttaacaac cgaagtaacc cgcaatgcgg aagggcgagg ggattgcgag tcaccgagtt      60
tcccgcgcgg cttgagtcac ggcctagaaa gagagatgtt gggggttccca ggaccaggac    120
```

-continued

```
2701 ATGGAGAGTGAGATGATGGAGATCTTGTCAGTGCTAGCTAAGGGTGACCACAGCCCTGTC
 901 -M--E--S--E--M--M--E--I--L--S--V--L--A--K--G--D--H--S--P--V-

2761 ACAAGGGCTGCTGCAGCCTGCCTGGACAAAGCAGTGGAATATGGGCTTATCCAACCCAAC
 921 -T--R--A--A--A--A--C--L--D--K--A--V--E--Y--G--L--I--Q--P--N-

2821 CAAGATGGAGAGTGA
 941 -Q--D--G--E--*-
```

SEQUENCE LISTING

```
<160> NUMBER OF SEQ ID NOS: 27

<210> SEQ ID NO 1
<211> LENGTH: 3625
<212> TYPE: DNA
<213> ORGANISM: Homo sapiens
<220> FEATURE:
<221> NAME/KEY: CDS
<222> LOCATION: (836)..(3622)

<400> SEQUENCE: 1
acttaacaac cgaagtaacc cgcaatgcgg aagggcgagg ggattgcgag tcaccgagtt      60
tcccgcgcgg cttgagtcac ggcctagaaa gagagatgtt ggggttccca ggaccaggac     120
agaggtggta gtgaactctc atgggcatcc agagaaggtc aggccccttg ctgacaggcc     180
tatctgtggg gctactgctg ctcttcagct gggtgaccct tgtccagcca acctctctct     240
cagctctggt ccaccaccct cacttgtgcc agaccacccg ggatgtccat ggccgtcact     300
accctggttt cttttgccct cgtctgtctg attctccaga ggaagcctac tgctgccacc     360
tgcaggctgc agggggctcc tgctgcaccc gggctgaatt tgaggccctg taccaagtca     420
atctgtccgc tcttccgccc cgcccatcc tcaggggccc aggcccgctc ctagtgctgg      480
gcctctacaa cctactggtt gtgaccctga tgaccgtaga cctcgtgcac ttctgctgcg     540
gtcggggccg gagtctgggc tggagccacc gcaggcctcc ctctgggtcc tccgccgcga     600
gctccctgca ggtctctgcg ggacagctt aggtgcgccc ggagcttgcc tgcacctgcg     660
atccagagcc aagcgccccg cccctgcccg ggcgcgctcc ctccttagcc ctgcccctct     720
ctgaccccac ctccgacgca agagtggggc ggggcagctg ccggtggcgt cccgaaccca     780
gactcgcccc gccccagaga ctgcgcctgc gcgggcacga acaacctct ccgcg atg       838
                                                                 Met
                                                                  1 act gcc agc tca gtg gag cag ctg cgg aag gag ggc aat gag ctg ttc      886
Thr Ala Ser Ser Val Glu Gln Leu Arg Lys Glu Gly Asn Glu Leu Phe
         5                  10                  15 aaa tgt gga gac tac ggg ggc gcc ctg gcg gcc tac act cag gcc ctg      934
Lys Cys Gly Asp Tyr Gly Gly Ala Leu Ala Ala Tyr Thr Gln Ala Leu
     20                  25                  30 ggt ctg gac gcg acg ccc cag gac cag gcc gtt ctg cac cgg aac cgg      982
Gly Leu Asp Ala Thr Pro Gln Asp Gln Ala Val Leu His Arg Asn Arg
 35                  40                  45 gcc gcc tgc cac ctc aag ctg gaa gat tac gac aaa gca gaa aca gag     1030
Ala Ala Cys His Leu Lys Leu Glu Asp Tyr Asp Lys Ala Glu Thr Glu
 50                  55                  60                  65 gca tcc aaa gcc att gaa aag gat ggt ggg gat gtc aaa gca ctc tac     1078
Ala Ser Lys Ala Ile Glu Lys Asp Gly Gly Asp Val Lys Ala Leu Tyr
                 70                  75                  80 cgg cgg agc caa gcc cta gag aag ctg ggc cgc ctg gac cag gct gtc     1126
Arg Arg Ser Gln Ala Leu Glu Lys Leu Gly Arg Leu Asp Gln Ala Val
             85                  90                  95
```

-continued

| | |
|---|---|
| ctt gac ctg cag aga tgt gtg agc ttg gag ccc aag aac aaa gtt ttc<br>Leu Asp Leu Gln Arg Cys Val Ser Leu Glu Pro Lys Asn Lys Val Phe<br>100           105           110 | 1174 |
| cag gag gcc ttg cgg aac atc ggg ggc cag att cag gag aag gtg cga<br>Gln Glu Ala Leu Arg Asn Ile Gly Gly Gln Ile Gln Glu Lys Val Arg<br>115           120           125 | 1222 |
| tac atg tcc tcg acg gat gcc aaa gtg gaa cag atg ttt cag ata ctg<br>Tyr Met Ser Ser Thr Asp Ala Lys Val Glu Gln Met Phe Gln Ile Leu<br>130           135           140           145 | 1270 |
| ttg gac cca gaa gag aag ggc act gag aaa aag caa aag gct tct cag<br>Leu Asp Pro Glu Glu Lys Gly Thr Glu Lys Lys Gln Lys Ala Ser Gln<br>150           155           160 | 1318 |
| aac ctg gtg gtg ctg gcc agg gag gat gct gga gcg gag aag atc ttc<br>Asn Leu Val Val Leu Ala Arg Glu Asp Ala Gly Ala Glu Lys Ile Phe<br>165           170           175 | 1366 |
| cgg agt aat ggg gtt cag ctc ttg caa cgt tta ctg gac atg gga gag<br>Arg Ser Asn Gly Val Gln Leu Leu Gln Arg Leu Leu Asp Met Gly Glu<br>180           185           190 | 1414 |
| act gac ctc atg ctg gcg gct ctc cgt acg ctg gtt ggc att tgc tct<br>Thr Asp Leu Met Leu Ala Ala Leu Arg Thr Leu Val Gly Ile Cys Ser<br>195           200           205 | 1462 |
| gag cat cag tca cgg aca gtg gca acc ctg agc ata ctg gga act cgg<br>Glu His Gln Ser Arg Thr Val Ala Thr Leu Ser Ile Leu Gly Thr Arg<br>210           215           220           225 | 1510 |
| cga gta gtc tcc atc ctg ggc gtg gaa agc cag gct gtg tcc ctg gct<br>Arg Val Val Ser Ile Leu Gly Val Glu Ser Gln Ala Val Ser Leu Ala<br>230           235           240 | 1558 |
| gcc tgc cac ctg ctg cag gtt atg ttt gat gcc ctc aag gaa ggt gtc<br>Ala Cys His Leu Leu Gln Val Met Phe Asp Ala Leu Lys Glu Gly Val<br>245           250           255 | 1606 |
| aaa aaa ggc ttc cga ggc aaa gaa ggt gcc atc att gtg gat cct gcc<br>Lys Lys Gly Phe Arg Gly Lys Glu Gly Ala Ile Ile Val Asp Pro Ala<br>260           265           270 | 1654 |
| cgg gag ctg aag gtc ctc atc agt aac ctc tta gat ctg ctg aca gag<br>Arg Glu Leu Lys Val Leu Ile Ser Asn Leu Leu Asp Leu Leu Thr Glu<br>275           280           285 | 1702 |
| gtg ggg gtc tct ggc caa ggc cga gac aat gcc ctg acc ctc ctg att<br>Val Gly Val Ser Gly Gln Gly Arg Asp Asn Ala Leu Thr Leu Leu Ile<br>290           295           300           305 | 1750 |
| aaa gcg gtg ccc cgg aag tct ctc aag gac ccc aac aac agc ctc acc<br>Lys Ala Val Pro Arg Lys Ser Leu Lys Asp Pro Asn Asn Ser Leu Thr<br>310           315           320 | 1798 |
| ctc tgg gtc atc gac caa ggt ctg aaa aag att ttg gaa gtg ggg ggc<br>Leu Trp Val Ile Asp Gln Gly Leu Lys Lys Ile Leu Glu Val Gly Gly<br>325           330           335 | 1846 |
| tct cta cag gac cct cct ggg gag ctc gca gtg acc gca aac agc cgc<br>Ser Leu Gln Asp Pro Pro Gly Glu Leu Ala Val Thr Ala Asn Ser Arg<br>340           345           350 | 1894 |
| atg agc gcc tct att ctc ctc agc aag ctc ttt gat gac ctc aag tgt<br>Met Ser Ala Ser Ile Leu Leu Ser Lys Leu Phe Asp Asp Leu Lys Cys<br>355           360           365 | 1942 |
| gat gcg gag agg gag aat ttc cac aga ctt tgt gaa aac tac atc aag<br>Asp Ala Glu Arg Glu Asn Phe His Arg Leu Cys Glu Asn Tyr Ile Lys<br>370           375           380           385 | 1990 |
| agc tgg ttt gag ggc caa ggg ctg gcc ggg aag cta cgg gcc atc cag<br>Ser Trp Phe Glu Gly Gln Gly Leu Ala Gly Lys Leu Arg Ala Ile Gln<br>390           395           400 | 2038 |
| acg gtg tcc tgc ctc ctg cag ggc cca tgt gac gct ggc aac cgg gcc<br>Thr Val Ser Cys Leu Leu Gln Gly Pro Cys Asp Ala Gly Asn Arg Ala<br>405           410           415 | 2086 |

| | |
|---|---:|
| ttg gag ctg agc ggt gtc atg gag agt gtg att gct ctg tgt gcc tct<br>Leu Glu Leu Ser Gly Val Met Glu Ser Val Ile Ala Leu Cys Ala Ser<br>420 425 430 | 2134 |
| gag cag gag gag gag cag ctg gtg gcc gtg gag gct ctg atc cat gca<br>Glu Gln Glu Glu Glu Gln Leu Val Ala Val Glu Ala Leu Ile His Ala<br>435 440 445 | 2182 |
| gcc ggc aag gct aag cgg gcc tca ttc atc act gcc aat ggt gtc tcg<br>Ala Gly Lys Ala Lys Arg Ala Ser Phe Ile Thr Ala Asn Gly Val Ser<br>450 455 460 465 | 2230 |
| ctg ctg aag gac cta tat aag tgc agc gag aag gac agc atc cgc atc<br>Leu Leu Lys Asp Leu Tyr Lys Cys Ser Glu Lys Asp Ser Ile Arg Ile<br>470 475 480 | 2278 |
| cgg gcg cta gtg gga ctc tgt aag ctc ggt tcg gct gga ggg act gac<br>Arg Ala Leu Val Gly Leu Cys Lys Leu Gly Ser Ala Gly Gly Thr Asp<br>485 490 495 | 2326 |
| ttc agc atg aag cag ttt gct gaa ggc tcc act ctc aaa ctg gct aag<br>Phe Ser Met Lys Gln Phe Ala Glu Gly Ser Thr Leu Lys Leu Ala Lys<br>500 505 510 | 2374 |
| cag tgt cga aag tgg ctg tgc aat gac cag atc gac gca ggc act cgg<br>Gln Cys Arg Lys Trp Leu Cys Asn Asp Gln Ile Asp Ala Gly Thr Arg<br>515 520 525 | 2422 |
| cgc tgg gca gtg gag ggc ctg gct tac ctg acc ttt gat gcc gac gtg<br>Arg Trp Ala Val Glu Gly Leu Ala Tyr Leu Thr Phe Asp Ala Asp Val<br>530 535 540 545 | 2470 |
| aag gaa gag ttt gtg gag gat gcg gct gct ctg aaa gct ctg ttc cag<br>Lys Glu Glu Phe Val Glu Asp Ala Ala Ala Leu Lys Ala Leu Phe Gln<br>550 555 560 | 2518 |
| ctc agc agg ttg gag gag agg tca gtg ctc ttt gcg gtg gcc tca gcg<br>Leu Ser Arg Leu Glu Glu Arg Ser Val Leu Phe Ala Val Ala Ser Ala<br>565 570 575 | 2566 |
| ctg gtg aac tgc acc aac agc tat gac tac gag gag ccc gac ccc aag<br>Leu Val Asn Cys Thr Asn Ser Tyr Asp Tyr Glu Glu Pro Asp Pro Lys<br>580 585 590 | 2614 |
| atg gtg gag ctg gcc aag tat gcc aag cag cat gtg ccc gag cag cac<br>Met Val Glu Leu Ala Lys Tyr Ala Lys Gln His Val Pro Glu Gln His<br>595 600 605 | 2662 |
| ccc aag gac aag cca agc ttc gtg cgg gct cgg gtg aag aag ctg ctg<br>Pro Lys Asp Lys Pro Ser Phe Val Arg Ala Arg Val Lys Lys Leu Leu<br>610 615 620 625 | 2710 |
| gca gcg ggt gtg gtg tcg gcc atg gtg tgc atg gtg aag acg gag agc<br>Ala Ala Gly Val Val Ser Ala Met Val Cys Met Val Lys Thr Glu Ser<br>630 635 640 | 2758 |
| cct gtg ctg acc agt tcc tgc aga gag ctg ctc tcc agg gtc ttc ttg<br>Pro Val Leu Thr Ser Ser Cys Arg Glu Leu Leu Ser Arg Val Phe Leu<br>645 650 655 | 2806 |
| gct tta gtg gaa gag gta gag gac cga ggc act gtg gtt gcc cag gga<br>Ala Leu Val Glu Glu Val Glu Asp Arg Gly Thr Val Val Ala Gln Gly<br>660 665 670 | 2854 |
| ggc ggc agg gcg ctg atc ccg ctg gcc ctg gaa ggc acg gac gtg ggg<br>Gly Gly Arg Ala Leu Ile Pro Leu Ala Leu Glu Gly Thr Asp Val Gly<br>675 680 685 | 2902 |
| cag aca aag gca gcc cag gcc ctt gcc aag ctc acc atc acc tcc aac<br>Gln Thr Lys Ala Ala Gln Ala Leu Ala Lys Leu Thr Ile Thr Ser Asn<br>690 695 700 705 | 2950 |
| ccg gag atg acc ttc cct ggc gag cgg atc tat gag gtg gtc cgg ccc<br>Pro Glu Met Thr Phe Pro Gly Glu Arg Ile Tyr Glu Val Val Arg Pro<br>710 715 720 | 2998 |
| ctc gtc tcc ctg ttg cac ctc aac tgc tca ggc ctg cag aac ttc gag<br>Leu Val Ser Leu Leu His Leu Asn Cys Ser Gly Leu Gln Asn Phe Glu | 3046 |

-continued

```
                725                 730                 735
gcg ctc atg gcc cta aca aac ctg gct ggg atc agc gag agg ctc cgg       3094
Ala Leu Met Ala Leu Thr Asn Leu Ala Gly Ile Ser Glu Arg Leu Arg
            740                 745                 750 cag aag atc ctg aag gag aag gct gtg ccc atg ata gaa ggc tac atg       3142
Gln Lys Ile Leu Lys Glu Lys Ala Val Pro Met Ile Glu Gly Tyr Met
755                 760                 765 ttt gag gag cat gag atg atc cgc cgg gca gcc acg gag tgc atg tgt       3190
Phe Glu Glu His Glu Met Ile Arg Arg Ala Ala Thr Glu Cys Met Cys
770                 775                 780                 785 aac ttg gcc atg agc aag gag gtg cag gac ctc ttc gaa gcc cag ggc       3238
Asn Leu Ala Met Ser Lys Glu Val Gln Asp Leu Phe Glu Ala Gln Gly
                790                 795                 800 aat gac cga ctg aag ctg ctg gtg ctg tac agt gga gag gat gat gag       3286
Asn Asp Arg Leu Lys Leu Leu Val Leu Tyr Ser Gly Glu Asp Asp Glu
            805                 810                 815 ctg cta cag cgg gca gct gcc ggg ggc ttg gcc atg ctt acc tcc atg       3334
Leu Leu Gln Arg Ala Ala Ala Gly Gly Leu Ala Met Leu Thr Ser Met
        820                 825                 830 cgg ccc acg ctc tgc agc cgc att ccc caa gtg acc aca cac tgg ctg       3382
Arg Pro Thr Leu Cys Ser Arg Ile Pro Gln Val Thr Thr His Trp Leu
835                 840                 845 gag atc ctg cag gcc ctg ctt ctg agc tcc aac cag gag ctg cag cac       3430
Glu Ile Leu Gln Ala Leu Leu Leu Ser Ser Asn Gln Glu Leu Gln His
850                 855                 860                 865 cgg ggt gct gtg gtg gtg ctg aac atg gtg gag gcc tcg agg gag att       3478
Arg Gly Ala Val Val Val Leu Asn Met Val Glu Ala Ser Arg Glu Ile
                870                 875                 880 gcc agc acc ctg atg gag agt gag atg atg gag atc ttg tca gtg cta       3526
Ala Ser Thr Leu Met Glu Ser Glu Met Met Glu Ile Leu Ser Val Leu
            885                 890                 895 gct aag ggt gac cac agc cct gtc aca agg gct gct gca gcc tgc ctg       3574
Ala Lys Gly Asp His Ser Pro Val Thr Arg Ala Ala Ala Ala Cys Leu
        900                 905                 910 gac aaa gca gtg gaa tat ggg ctt atc caa ccc aac caa gat gga gag       3622
Asp Lys Ala Val Glu Tyr Gly Leu Ile Gln Pro Asn Gln Asp Gly Glu
915                 920                 925 tga                                                                   3625

<210> SEQ ID NO 2
<211> LENGTH: 2835
<212> TYPE: DNA
<213> ORGANISM: Homo sapiens
<220> FEATURE:
<221> NAME/KEY: CDS
<222> LOCATION: (1)..(2832)

<400> SEQUENCE: 2 atg act gtg agt ggt cca ggg acc ccc gag ccc cgg ccg gcc acc ccc        48
Met Thr Val Ser Gly Pro Gly Thr Pro Glu Pro Arg Pro Ala Thr Pro
1               5                   10                  15 ggg gcc agc tca gtg gag cag ctg cgg aag gag ggc aat gag ctg ttc        96
Gly Ala Ser Ser Val Glu Gln Leu Arg Lys Glu Gly Asn Glu Leu Phe
            20                  25                  30 aaa tgt gga gac tac ggg ggc gcc ctg gcg gcc tac act cag gcc ctg       144
Lys Cys Gly Asp Tyr Gly Gly Ala Leu Ala Ala Tyr Thr Gln Ala Leu
        35                  40                  45 ggt ctg gac gcg acg ccc cag gac cag gcc gtt ctg cac cgg aac cgg       192
Gly Leu Asp Ala Thr Pro Gln Asp Gln Ala Val Leu His Arg Asn Arg
    50                  55                  60
```

| | | |
|---|---|---|
| gcc gcc tgc cac ctc aag ctg gaa gat tac gac aaa gca gaa aca gag<br>Ala Ala Cys His Leu Lys Leu Glu Asp Tyr Asp Lys Ala Glu Thr Glu<br>65                           70                   75                  80 | | 240 |
| gca tcc aaa gcc att gaa aag gat ggt ggg gat gtc aaa gca ctc tac<br>Ala Ser Lys Ala Ile Glu Lys Asp Gly Gly Asp Val Lys Ala Leu Tyr<br>                85                   90                   95 | | 288 |
| cgg cgg agc caa gcc cta gag aag ctg ggc cgc ctg gac cag gct gtc<br>Arg Arg Ser Gln Ala Leu Glu Lys Leu Gly Arg Leu Asp Gln Ala Val<br>              100               105              110 | | 336 |
| ctt gac ctg cag aga tgt gtg agc ttg gag ccc aag aac aaa gtt ttc<br>Leu Asp Leu Gln Arg Cys Val Ser Leu Glu Pro Lys Asn Lys Val Phe<br>              115               120              125 | | 384 |
| cag gag gcc ttg cgg aac atc ggg ggc cag att cag gag aag gtg cga<br>Gln Glu Ala Leu Arg Asn Ile Gly Gly Gln Ile Gln Glu Lys Val Arg<br>130                   135              140 | | 432 |
| tac atg tcc tcg acg gat gcc aaa gtg gaa cag atg ttt cag ata ctg<br>Tyr Met Ser Ser Thr Asp Ala Lys Val Glu Gln Met Phe Gln Ile Leu<br>145                       150               155              160 | | 480 |
| ttg gac cca gaa gag aag ggc act gag aaa aag caa aag gct tct cag<br>Leu Asp Pro Glu Glu Lys Gly Thr Glu Lys Lys Gln Lys Ala Ser Gln<br>                165               170              175 | | 528 |
| aac ctg gtg gtg ctg gcc agg gag gat gct gga gcg gag aag atc ttc<br>Asn Leu Val Val Leu Ala Arg Glu Asp Ala Gly Ala Glu Lys Ile Phe<br>              180               185              190 | | 576 |
| cgg agt aat ggg gtt cag ctc ttg caa cgt tta ctg gac atg gga gag<br>Arg Ser Asn Gly Val Gln Leu Leu Gln Arg Leu Leu Asp Met Gly Glu<br>             195               200              205 | | 624 |
| act gac ctc atg ctg gcg gct ctg cgt acg ctg gtt ggc att tgc tct<br>Thr Asp Leu Met Leu Ala Ala Leu Arg Thr Leu Val Gly Ile Cys Ser<br>210                       215               220 | | 672 |
| gag cat cag tca cgg aca gtg gca acc ctg agc ata ctg gga act cgg<br>Glu His Gln Ser Arg Thr Val Ala Thr Leu Ser Ile Leu Gly Thr Arg<br>225                       230              235              240 | | 720 |
| cga gta gtc tcc atc ctg ggc gtg gaa agc cag gct gtg tcc ctg gct<br>Arg Val Val Ser Ile Leu Gly Val Glu Ser Gln Ala Val Ser Leu Ala<br>                245               250              255 | | 768 |
| gcc tgc cac ctg ctg cag gtt atg ttt gat gcc ctc aag gaa ggt gtc<br>Ala Cys His Leu Leu Gln Val Met Phe Asp Ala Leu Lys Glu Gly Val<br>              260               265              270 | | 816 |
| aaa aaa ggc ttc cga ggc aaa gaa ggt gcc atc att gtg gat cct gcc<br>Lys Lys Gly Phe Arg Gly Lys Glu Gly Ala Ile Ile Val Asp Pro Ala<br>           275               280              285 | | 864 |
| cgg gag ctg aag gtc ctc atc agt aac ctc tta gat ctg ctg aca gag<br>Arg Glu Leu Lys Val Leu Ile Ser Asn Leu Leu Asp Leu Leu Thr Glu<br>290                       295              300 | | 912 |
| gtg ggg gtc tct ggc caa ggc cga gac aat gcc ctg acc ctc ctg att<br>Val Gly Val Ser Gly Gln Gly Arg Asp Asn Ala Leu Thr Leu Leu Ile<br>305                       310              315              320 | | 960 |
| aaa gcg gtg ccc cgg aag tct ctc aag gac ccc aac aac agc ctc acc<br>Lys Ala Val Pro Arg Lys Ser Leu Lys Asp Pro Asn Asn Ser Leu Thr<br>              325               330              335 | | 1008 |
| ctc tgg gtc atc gac caa ggt ctg aaa aag att ttg gaa gtg ggg ggc<br>Leu Trp Val Ile Asp Gln Gly Leu Lys Lys Ile Leu Glu Val Gly Gly<br>              340               345              350 | | 1056 |
| tct cta cag gac cct cct ggg gag ctc gca gtg acc gca aac agc cgc<br>Ser Leu Gln Asp Pro Pro Gly Glu Leu Ala Val Thr Ala Asn Ser Arg<br>           355               360              365 | | 1104 |
| atg agc gcc tct att ctc ctc agc aag ctc ttt gat gac ctc aag tgt<br>Met Ser Ala Ser Ile Leu Leu Ser Lys Leu Phe Asp Asp Leu Lys Cys<br>370                       375              380 | | 1152 |

```
gat gcg gag agg gag aat ttc cac aga ctt tgt gaa aac tac atc aag    1200
Asp Ala Glu Arg Glu Asn Phe His Arg Leu Cys Glu Asn Tyr Ile Lys
385                 390                 395                 400 agc tgg ttt gag ggc caa ggg ctg gcc ggg aag cta cgg gcc atc cag    1248
Ser Trp Phe Glu Gly Gln Gly Leu Ala Gly Lys Leu Arg Ala Ile Gln
                405                 410                 415 acg gtg tcc tgc ctc ctg cag ggc cca tgt gac gct ggc aac cgg gcc    1296
Thr Val Ser Cys Leu Leu Gln Gly Pro Cys Asp Ala Gly Asn Arg Ala
420                 425                 430 ttg gag ctg agc ggt gtc atg gag agt gtg att gct ctg tgt gcc tct    1344
Leu Glu Leu Ser Gly Val Met Glu Ser Val Ile Ala Leu Cys Ala Ser
            435                 440                 445 gag cag gag gag gag cag ctg gtg gcc gtg gag gct ctg atc cat gca    1392
Glu Gln Glu Glu Glu Gln Leu Val Ala Val Glu Ala Leu Ile His Ala
450                 455                 460 gcc ggc aag gct aag cgg gcc tca ttc atc act gca aat ggt gtc tcg    1440
Ala Gly Lys Ala Lys Arg Ala Ser Phe Ile Thr Ala Asn Gly Val Ser
465                 470                 475                 480 ctg ctg aag gac cta tat aag tgc agc gag aag gac agc atc cgc atc    1488
Leu Leu Lys Asp Leu Tyr Lys Cys Ser Glu Lys Asp Ser Ile Arg Ile
                485                 490                 495 cgg gcg cta gtg gga ctc tgt aag ctc ggt tcg gct gga ggg act gac    1536
Arg Ala Leu Val Gly Leu Cys Lys Leu Gly Ser Ala Gly Gly Thr Asp
            500                 505                 510 ttc agc atg aag cag ttt gct gaa ggc tcc act ctc aaa ctg gct aag    1584
Phe Ser Met Lys Gln Phe Ala Glu Gly Ser Thr Leu Lys Leu Ala Lys
            515                 520                 525 cag tgt cga aag tgg ctg tgc aat gac cag atc gac gca ggc act cgg    1632
Gln Cys Arg Lys Trp Leu Cys Asn Asp Gln Ile Asp Ala Gly Thr Arg
530                 535                 540 cgc tgg gca gtg gag ggc ctg gct tac ctg acc ttt gat gcc gac gtg    1680
Arg Trp Ala Val Glu Gly Leu Ala Tyr Leu Thr Phe Asp Ala Asp Val
545                 550                 555                 560 aag gaa gag ttt gtg gag gat gcg gct gct ctg aaa gct ctg ttc cag    1728
Lys Glu Glu Phe Val Glu Asp Ala Ala Ala Leu Lys Ala Leu Phe Gln
                565                 570                 575 ctc agc agg ttg gag gag agg tca gtg ctc ttt gcg gtg gcc tca gcg    1776
Leu Ser Arg Leu Glu Glu Arg Ser Val Leu Phe Ala Val Ala Ser Ala
            580                 585                 590 ctg gtg aac tgc acc aac agc tat gac tac gag gag ccc gac ccc aag    1824
Leu Val Asn Cys Thr Asn Ser Tyr Asp Tyr Glu Glu Pro Asp Pro Lys
            595                 600                 605 atg gtg gag ctg gcc aag tat gcc aag cag cat gtg ccc gag cag cac    1872
Met Val Glu Leu Ala Lys Tyr Ala Lys Gln His Val Pro Glu Gln His
610                 615                 620 ccc aag gac aag cca agc ttc gtg cgg gct cgg gtg aag aag ctg ctg    1920
Pro Lys Asp Lys Pro Ser Phe Val Arg Ala Arg Val Lys Lys Leu Leu
625                 630                 635                 640 gca gcg ggt gtg gtg tcg gcc atg gtg tgc atg gtg aag acg gag agc    1968
Ala Ala Gly Val Val Ser Ala Met Val Cys Met Val Lys Thr Glu Ser
                645                 650                 655 cct gtg ctg acc agt tcc tgc aga gag ctg ctc tcc agg gtc ttc ttg    2016
Pro Val Leu Thr Ser Ser Cys Arg Glu Leu Leu Ser Arg Val Phe Leu
            660                 665                 670 gct tta gtg gaa gag gta gag gac cga ggc act gtg gtt gcc cag gga    2064
Ala Leu Val Glu Glu Val Glu Asp Arg Gly Thr Val Val Ala Gln Gly
            675                 680                 685 ggc ggc agg gcg ctg atc ccg ctg gcc ctg gaa ggc acg gac gtg ggg    2112
Gly Gly Arg Ala Leu Ile Pro Leu Ala Leu Glu Gly Thr Asp Val Gly
```

```
                     690                  695                  700
cag aca aag gca gcc cag gcc ctt gcc aag ctc acc atc acc tcc aac      2160
Gln Thr Lys Ala Ala Gln Ala Leu Ala Lys Leu Thr Ile Thr Ser Asn
705                 710                 715                 720 ccg gag atg acc ttc cct ggc gag cgg atc tat gag gtg gtc cgg ccc      2208
Pro Glu Met Thr Phe Pro Gly Glu Arg Ile Tyr Glu Val Val Arg Pro
                725                 730                 735 ctc gtc tcc ctg ttg cac ctc aac tgc tca ggc ctg cag aac ttc gag      2256
Leu Val Ser Leu Leu His Leu Asn Cys Ser Gly Leu Gln Asn Phe Glu
            740                 745                 750 gcg ctc atg gcc cta aca aac ctg gct ggg atc agc gag agg ctc cgg      2304
Ala Leu Met Ala Leu Thr Asn Leu Ala Gly Ile Ser Glu Arg Leu Arg
        755                 760                 765 cag aag atc ctg aag gag aag gct gtg ccc atg ata gaa ggc tac atg      2352
Gln Lys Ile Leu Lys Glu Lys Ala Val Pro Met Ile Glu Gly Tyr Met
    770                 775                 780 ttt gag gag cat gag atg atc cgc cgg gca gcc acg gag tgc atg tgt      2400
Phe Glu Glu His Glu Met Ile Arg Arg Ala Ala Thr Glu Cys Met Cys
785                 790                 795                 800 aac ttg gcc atg agc aag gag gtg cag gac ctc ttc gaa gcc cag ggc      2448
Asn Leu Ala Met Ser Lys Glu Val Gln Asp Leu Phe Glu Ala Gln Gly
                805                 810                 815 aat gac cga ctg aag ctg ctg gtg ctg tac agt gga gag gat gat gag      2496
Asn Asp Arg Leu Lys Leu Leu Val Leu Tyr Ser Gly Glu Asp Asp Glu
            820                 825                 830 ctg cta cag cgg gca gct gcc ggg ggc ttg gcc atg ctt acc tcc atg      2544
Leu Leu Gln Arg Ala Ala Ala Gly Gly Leu Ala Met Leu Thr Ser Met
        835                 840                 845 cgg ccc acg ctc tgc agc cgc att ccc caa gtg acc aca cac tgg ctg      2592
Arg Pro Thr Leu Cys Ser Arg Ile Pro Gln Val Thr Thr His Trp Leu
    850                 855                 860 gag atc ctg cag gcc ctg ctt ctg agc tcc aac cag gag ctg cag cac      2640
Glu Ile Leu Gln Ala Leu Leu Leu Ser Ser Asn Gln Glu Leu Gln His
865                 870                 875                 880 cgg ggt gct gtg gtg gtg ctg aac atg gtg gag gcc tcg agg gag att      2688
Arg Gly Ala Val Val Val Leu Asn Met Val Glu Ala Ser Arg Glu Ile
                885                 890                 895 gcc agc acc ctg atg gag agt gag atg atg gag atc ttg tca gtg cta      2736
Ala Ser Thr Leu Met Glu Ser Glu Met Met Glu Ile Leu Ser Val Leu
            900                 905                 910 gct aag ggt gac cac agc cct gtc aca agg gct gct gca gcc tgc ctg      2784
Ala Lys Gly Asp His Ser Pro Val Thr Arg Ala Ala Ala Ala Cys Leu
        915                 920                 925 gac aaa gca gtg gaa tat ggg ctt atc caa ccc aac caa gat gga gag      2832
Asp Lys Ala Val Glu Tyr Gly Leu Ile Gln Pro Asn Gln Asp Gly Glu
    930                 935                 940 tga                                                                  2835

<210> SEQ ID NO 3
<211> LENGTH: 929
<212> TYPE: PRT
<213> ORGANISM: Homo sapiens

<400> SEQUENCE: 3

Met Thr Ala Ser Ser Val Glu Gln Leu Arg Lys Glu Gly Asn Glu Leu
1               5                   10                  15

Phe Lys Cys Gly Asp Tyr Gly Gly Ala Leu Ala Ala Tyr Thr Gln Ala
                20                  25                  30

Leu Gly Leu Asp Ala Thr Pro Gln Asp Gln Ala Val Leu His Arg Asn
```

```
                 35                  40                  45
Arg Ala Ala Cys His Leu Lys Leu Glu Asp Tyr Asp Lys Ala Glu Thr
 50                  55                  60
Glu Ala Ser Lys Ala Ile Glu Lys Asp Gly Gly Asp Val Lys Ala Leu
65                   70                  75                  80
Tyr Arg Arg Ser Gln Ala Leu Glu Lys Leu Gly Arg Leu Asp Gln Ala
                     85                  90                  95
Val Leu Asp Leu Gln Arg Cys Val Ser Leu Glu Pro Lys Asn Lys Val
                100                 105                 110
Phe Gln Glu Ala Leu Arg Asn Ile Gly Gly Gln Ile Gln Glu Lys Val
                115                 120                 125
Arg Tyr Met Ser Ser Thr Asp Ala Lys Val Glu Gln Met Phe Gln Ile
130                 135                 140
Leu Leu Asp Pro Glu Glu Lys Gly Thr Glu Lys Lys Gln Lys Ala Ser
145                 150                 155                 160
Gln Asn Leu Val Val Leu Ala Arg Glu Asp Ala Gly Ala Glu Lys Ile
                165                 170                 175
Phe Arg Ser Asn Gly Val Gln Leu Leu Gln Arg Leu Leu Asp Met Gly
                180                 185                 190
Glu Thr Asp Leu Met Leu Ala Ala Leu Arg Thr Leu Val Gly Ile Cys
                195                 200                 205
Ser Glu His Gln Ser Arg Thr Val Ala Thr Leu Ser Ile Leu Gly Thr
210                 215                 220
Arg Arg Val Val Ser Ile Leu Gly Val Glu Ser Gln Ala Val Ser Leu
225                 230                 235                 240
Ala Ala Cys His Leu Leu Gln Val Met Phe Asp Ala Leu Lys Glu Gly
                245                 250                 255
Val Lys Lys Gly Phe Arg Gly Lys Glu Gly Ala Ile Ile Val Asp Pro
                260                 265                 270
Ala Arg Glu Leu Lys Val Leu Ile Ser Asn Leu Leu Asp Leu Leu Thr
                275                 280                 285
Glu Val Gly Val Ser Gly Gln Gly Arg Asp Asn Ala Leu Thr Leu Leu
                290                 295                 300
Ile Lys Ala Val Pro Arg Lys Ser Leu Lys Asp Pro Asn Asn Ser Leu
305                 310                 315                 320
Thr Leu Trp Val Ile Asp Gln Gly Leu Lys Lys Ile Leu Glu Val Gly
                325                 330                 335
Gly Ser Leu Gln Asp Pro Pro Gly Glu Leu Ala Val Thr Ala Asn Ser
                340                 345                 350
Arg Met Ser Ala Ser Ile Leu Leu Ser Lys Leu Phe Asp Asp Leu Lys
                355                 360                 365
Cys Asp Ala Glu Arg Glu Asn Phe His Arg Leu Cys Glu Asn Tyr Ile
                370                 375                 380
Lys Ser Trp Phe Glu Gly Gln Gly Leu Ala Gly Lys Leu Arg Ala Ile
385                 390                 395                 400
Gln Thr Val Ser Cys Leu Leu Gln Gly Pro Cys Asp Ala Gly Asn Arg
                405                 410                 415
Ala Leu Glu Leu Ser Gly Val Met Glu Ser Val Ile Ala Leu Cys Ala
                420                 425                 430
Ser Glu Gln Glu Glu Glu Gln Leu Val Ala Val Glu Ala Leu Ile His
                435                 440                 445
Ala Ala Gly Lys Ala Lys Arg Ala Ser Phe Ile Thr Ala Asn Gly Val
450                 455                 460
```

```
Ser Leu Leu Lys Asp Leu Tyr Lys Cys Ser Glu Lys Asp Ser Ile Arg
465                 470                 475                 480

Ile Arg Ala Leu Val Gly Leu Cys Lys Leu Gly Ser Ala Gly Gly Thr
                    485                 490                 495

Asp Phe Ser Met Lys Gln Phe Ala Glu Gly Ser Thr Leu Lys Leu Ala
                500                 505                 510

Lys Gln Cys Arg Lys Trp Leu Cys Asn Asp Gln Ile Asp Ala Gly Thr
            515                 520                 525

Arg Arg Trp Ala Val Glu Gly Leu Ala Tyr Leu Thr Phe Asp Ala Asp
        530                 535                 540

Val Lys Glu Glu Phe Val Glu Asp Ala Ala Ala Leu Lys Ala Leu Phe
545                 550                 555                 560

Gln Leu Ser Arg Leu Glu Glu Arg Ser Val Leu Phe Ala Val Ala Ser
                565                 570                 575

Ala Leu Val Asn Cys Thr Asn Ser Tyr Asp Tyr Glu Glu Pro Asp Pro
                580                 585                 590

Lys Met Val Glu Leu Ala Lys Tyr Ala Lys Gln His Val Pro Glu Gln
            595                 600                 605

His Pro Lys Asp Lys Pro Ser Phe Val Arg Ala Arg Val Lys Lys Leu
        610                 615                 620

Leu Ala Ala Gly Val Val Ser Ala Met Val Cys Met Val Lys Thr Glu
625                 630                 635                 640

Ser Pro Val Leu Thr Ser Ser Cys Arg Glu Leu Leu Ser Arg Val Phe
                645                 650                 655

Leu Ala Leu Val Glu Glu Val Glu Asp Arg Gly Thr Val Val Ala Gln
                660                 665                 670

Gly Gly Gly Arg Ala Leu Ile Pro Leu Ala Leu Glu Gly Thr Asp Val
            675                 680                 685

Gly Gln Thr Lys Ala Ala Gln Ala Leu Ala Lys Leu Thr Ile Thr Ser
        690                 695                 700

Asn Pro Glu Met Thr Phe Pro Gly Glu Arg Ile Tyr Glu Val Val Arg
705                 710                 715                 720

Pro Leu Val Ser Leu Leu His Leu Asn Cys Ser Gly Leu Gln Asn Phe
                725                 730                 735

Glu Ala Leu Met Ala Leu Thr Asn Leu Ala Gly Ile Ser Glu Arg Leu
                740                 745                 750

Arg Gln Lys Ile Leu Lys Glu Lys Ala Val Pro Met Ile Glu Gly Tyr
            755                 760                 765

Met Phe Glu Glu His Glu Met Ile Arg Arg Ala Ala Thr Glu Cys Met
        770                 775                 780

Cys Asn Leu Ala Met Ser Lys Glu Val Gln Asp Leu Phe Glu Ala Gln
785                 790                 795                 800

Gly Asn Asp Arg Leu Lys Leu Leu Val Leu Tyr Ser Gly Glu Asp Asp
                805                 810                 815

Glu Leu Leu Gln Arg Ala Ala Ala Gly Gly Leu Ala Met Leu Thr Ser
                820                 825                 830

Met Arg Pro Thr Leu Cys Ser Arg Ile Pro Gln Val Thr Thr His Trp
            835                 840                 845

Leu Glu Ile Leu Gln Ala Leu Leu Leu Ser Ser Asn Gln Glu Leu Gln
        850                 855                 860

His Arg Gly Ala Val Val Val Leu Asn Met Val Glu Ala Ser Arg Glu
865                 870                 875                 880
```

```
Ile Ala Ser Thr Leu Met Glu Ser Glu Met Glu Ile Leu Ser Val
                885                 890                 895

Leu Ala Lys Gly Asp His Ser Pro Val Thr Arg Ala Ala Ala Cys
            900                 905                 910

Leu Asp Lys Ala Val Glu Tyr Gly Leu Ile Gln Pro Asn Gln Asp Gly
            915                 920                 925

Glu

<210> SEQ ID NO 4
<211> LENGTH: 944
<212> TYPE: PRT
<213> ORGANISM: Homo sapiens

<400> SEQUENCE: 4

Met Thr Val Ser Gly Pro Gly Thr Pro Glu Pro Arg Pro Ala Thr Pro
1               5                   10                  15

Gly Ala Ser Ser Val Glu Gln Leu Arg Lys Glu Gly Asn Glu Leu Phe
            20                  25                  30

Lys Cys Gly Asp Tyr Gly Gly Ala Leu Ala Ala Tyr Thr Gln Ala Leu
            35                  40                  45

Gly Leu Asp Ala Thr Pro Gln Asp Gln Ala Val Leu His Arg Asn Arg
    50                  55                  60

Ala Ala Cys His Leu Lys Leu Glu Asp Tyr Asp Lys Ala Glu Thr Glu
65                  70                  75                  80

Ala Ser Lys Ala Ile Glu Lys Asp Gly Gly Asp Val Lys Ala Leu Tyr
                85                  90                  95

Arg Arg Ser Gln Ala Leu Glu Lys Leu Gly Arg Leu Asp Gln Ala Val
            100                 105                 110

Leu Asp Leu Gln Arg Cys Val Ser Leu Glu Pro Lys Asn Lys Val Phe
            115                 120                 125

Gln Glu Ala Leu Arg Asn Ile Gly Gly Gln Ile Gln Glu Lys Val Arg
        130                 135                 140

Tyr Met Ser Ser Thr Asp Ala Lys Val Glu Gln Met Phe Gln Ile Leu
145                 150                 155                 160

Leu Asp Pro Glu Glu Lys Gly Thr Glu Lys Lys Gln Lys Ala Ser Gln
                165                 170                 175

Asn Leu Val Val Leu Ala Arg Glu Asp Ala Gly Ala Glu Lys Ile Phe
            180                 185                 190

Arg Ser Asn Gly Val Gln Leu Leu Gln Arg Leu Leu Asp Met Gly Glu
        195                 200                 205

Thr Asp Leu Met Leu Ala Ala Leu Arg Thr Leu Val Gly Ile Cys Ser
    210                 215                 220

Glu His Gln Ser Arg Thr Val Ala Thr Leu Ser Ile Leu Gly Thr Arg
225                 230                 235                 240

Arg Val Val Ser Ile Leu Gly Val Glu Ser Gln Ala Val Ser Leu Ala
                245                 250                 255

Ala Cys His Leu Leu Gln Val Met Phe Asp Ala Leu Lys Glu Gly Val
            260                 265                 270

Lys Lys Gly Phe Arg Gly Lys Glu Gly Ala Ile Ile Val Asp Pro Ala
        275                 280                 285

Arg Glu Leu Lys Val Leu Ile Ser Asn Leu Leu Asp Leu Leu Thr Glu
    290                 295                 300

Val Gly Val Ser Gly Gln Gly Arg Asp Asn Ala Leu Thr Leu Leu Ile
305                 310                 315                 320
```

```
Lys Ala Val Pro Arg Lys Ser Leu Lys Asp Pro Asn Asn Ser Leu Thr
                325                 330                 335
Leu Trp Val Ile Asp Gln Gly Leu Lys Lys Ile Leu Glu Val Gly Gly
            340                 345                 350
Ser Leu Gln Asp Pro Pro Gly Glu Leu Ala Val Thr Ala Asn Ser Arg
        355                 360                 365
Met Ser Ala Ser Ile Leu Leu Ser Lys Leu Phe Asp Asp Leu Lys Cys
    370                 375                 380
Asp Ala Glu Arg Glu Asn Phe His Arg Leu Cys Glu Asn Tyr Ile Lys
385                 390                 395                 400
Ser Trp Phe Glu Gly Gln Gly Leu Ala Gly Lys Leu Arg Ala Ile Gln
                405                 410                 415
Thr Val Ser Cys Leu Leu Gln Gly Pro Cys Asp Ala Gly Asn Arg Ala
            420                 425                 430
Leu Glu Leu Ser Gly Val Met Glu Ser Val Ile Ala Leu Cys Ala Ser
        435                 440                 445
Glu Gln Glu Glu Glu Gln Leu Val Ala Val Glu Ala Leu Ile His Ala
    450                 455                 460
Ala Gly Lys Ala Lys Arg Ala Ser Phe Ile Thr Ala Asn Gly Val Ser
465                 470                 475                 480
Leu Leu Lys Asp Leu Tyr Lys Cys Ser Glu Lys Asp Ser Ile Arg Ile
                485                 490                 495
Arg Ala Leu Val Gly Leu Cys Lys Leu Gly Ser Ala Gly Thr Asp
            500                 505                 510
Phe Ser Met Lys Gln Phe Ala Glu Gly Ser Thr Leu Lys Leu Ala Lys
        515                 520                 525
Gln Cys Arg Lys Trp Leu Cys Asn Asp Gln Ile Asp Ala Gly Thr Arg
    530                 535                 540
Arg Trp Ala Val Glu Gly Leu Ala Tyr Leu Thr Phe Asp Ala Asp Val
545                 550                 555                 560
Lys Glu Glu Phe Val Glu Asp Ala Ala Ala Leu Lys Ala Leu Phe Gln
                565                 570                 575
Leu Ser Arg Leu Glu Glu Arg Ser Val Leu Phe Ala Val Ala Ser Ala
            580                 585                 590
Leu Val Asn Cys Thr Asn Ser Tyr Asp Tyr Glu Glu Pro Asp Pro Lys
        595                 600                 605
Met Val Glu Leu Ala Lys Tyr Ala Lys Gln His Val Pro Glu Gln His
    610                 615                 620
Pro Lys Asp Lys Pro Ser Phe Val Arg Ala Arg Val Lys Lys Leu Leu
625                 630                 635                 640
Ala Ala Gly Val Val Ser Ala Met Val Cys Met Val Lys Thr Glu Ser
                645                 650                 655
Pro Val Leu Thr Ser Ser Cys Arg Glu Leu Leu Ser Arg Val Phe Leu
            660                 665                 670
Ala Leu Val Glu Glu Val Glu Asp Arg Gly Thr Val Val Ala Gln Gly
        675                 680                 685
Gly Gly Arg Ala Leu Ile Pro Leu Ala Leu Glu Gly Thr Asp Val Gly
    690                 695                 700
Gln Thr Lys Ala Ala Gln Ala Leu Ala Lys Leu Thr Ile Thr Ser Asn
705                 710                 715                 720
Pro Glu Met Thr Phe Pro Gly Glu Arg Ile Tyr Glu Val Val Arg Pro
                725                 730                 735
Leu Val Ser Leu Leu His Leu Asn Cys Ser Gly Leu Gln Asn Phe Glu
```

```
                   740                 745                 750
Ala Leu Met Ala Leu Thr Asn Leu Ala Gly Ile Ser Glu Arg Leu Arg
            755                 760                 765

Gln Lys Ile Leu Lys Glu Lys Ala Val Pro Met Ile Glu Gly Tyr Met
        770                 775                 780

Phe Glu Glu His Glu Met Ile Arg Arg Ala Ala Thr Glu Cys Met Cys
785                 790                 795                 800

Asn Leu Ala Met Ser Lys Glu Val Gln Asp Leu Phe Glu Ala Gln Gly
                805                 810                 815

Asn Asp Arg Leu Lys Leu Leu Val Leu Tyr Ser Gly Glu Asp Asp Glu
            820                 825                 830

Leu Leu Gln Arg Ala Ala Ala Gly Gly Leu Ala Met Leu Thr Ser Met
        835                 840                 845

Arg Pro Thr Leu Cys Ser Arg Ile Pro Gln Val Thr Thr His Trp Leu
    850                 855                 860

Glu Ile Leu Gln Ala Leu Leu Leu Ser Ser Asn Gln Glu Leu Gln His
865                 870                 875                 880

Arg Gly Ala Val Val Val Leu Asn Met Val Glu Ala Ser Arg Glu Ile
                885                 890                 895

Ala Ser Thr Leu Met Glu Ser Glu Met Met Glu Ile Leu Ser Val Leu
            900                 905                 910

Ala Lys Gly Asp His Ser Pro Val Thr Arg Ala Ala Ala Cys Leu
        915                 920                 925

Asp Lys Ala Val Glu Tyr Gly Leu Ile Gln Pro Asn Gln Asp Gly Glu
    930                 935                 940

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
tggccgtcac taccctggtt tcttt                                         25

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
ggacagaggt ggtagtgaac t                                             21

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
ggtccaggga ccccgagcc ccg                                            23

<210> SEQ ID NO 8
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 8
gtgagtggtc cagggacccc                                              20

<210> SEQ ID NO 9
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 9
uggccgucac uacccugguu ucuuu                                        25

<210> SEQ ID NO 10
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 10 aaagaaaacca ggguagugac ggcca                                       25

<210> SEQ ID NO 11
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 11
gguccaggga ccccgagcc ccg                                           23

<210> SEQ ID NO 12
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 12
cggggcucgg ggucccugg acc                                           23

<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 13
gtggtagtga actctcatg                                               19

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 14
accgaagtaa cccgcaatg                                               19
```

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
gagtcacggc ctagaaaga                                         19

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 16
aggacagagg tggtagtga                                         19

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 17
gacagaggtg gtagtgaac                                         19

<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 18
gctgaatttg aggccctgt                                         19

<210> SEQ ID NO 19
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 19
tgctgacagg cctatctgt                                         19

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20
gtctgattct ccagaggaa                                         19

<210> SEQ ID NO 21
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 21
cctctacaac ctactggtt                                                       19

<210> SEQ ID NO 22
<211> LENGTH: 15
<212> TYPE: PRT
<213> ORGANISM: Artificial Sequence
<220> FEATURE:
<223> OTHER INFORMATION: synthetic peptide

<400> SEQUENCE: 22

Val Ser Gly Pro Gly Thr Pro Glu Pro Arg Pro Ala Thr Pro Gly
1               5                   10                  15

<210> SEQ ID NO 23
<211> LENGTH: 3625
<212> TYPE: DNA
<213> ORGANISM: Homo sapiens

<400> SEQUENCE: 23
acttaacaac cgaagtaacc cgcaatgcgg aagggcgagg ggattgcgag tcaccgagtt    60
tcccgcgcgg cttgagtcac ggcctagaaa gagagatgtt ggggttccca ggaccaggac   120
agaggtggta gtgaactctc atgggcatcc agagaaggtc aggccccttg ctgacaggcc   180
tatctgtggg gctactgctg ctcttcagct gggtgaccct tgtccagcca acctctctct   240
cagctctggt ccaccaccct cacttgtgcc agaccacccg ggatgtccat ggccgtcact   300
accctggttt cttttgccct cgtctgtctg attctccaga ggaagcctac tgctgccacc   360
tgcaggctgc aggggctcc tgctgcaccc gggctgaatt tgaggccctg taccaagtca   420
atctgtccgc tcttccgccc ccgcccatcc tcagggccc aggcccgctc ctagtgctgg   480
gcctctacaa cctactggtt gtgaccctga tgaccgtaga cctcgtgcac ttctgctgcg   540
gtcggggccg gagtctgggc tggagccacc gcaggcctcc ctctgggtcc tccgccgcga   600
gctccctgca ggtctctgcg gggacagctt aggtgcgccc ggagcttgcc tgcacctgcg   660
atccagagcc aagcgccccg cccctgcccg ggcgcgctcc ctccttagcc ctgcccctct   720
ctgaccccac ctccgacgca agagtggggc ggggcagctg ccggtggcgt cccgaaccca   780
gactcgcccc gccccagaga ctgcgcctgc gcgggcacga acaacctct ccgcgatgac   840 tgccagctca gtggagcagc tgcggaagga gggcaatgag ctgttcaaat gtggagacta   900 cggggggcgcc ctggcggcct acactcaggc cctgggtctg gacgcgacgc ccaggacca   960 ggccgttctg caccggaacc gggccgcctg ccacctcaag ctggaagatt acgacaaagc  1020
agaaacagag gcatccaaag ccattgaaaa ggatggtggg gatgtcaaag cactctaccg  1080
gcggagccaa gccctagaga agctgggccg cctggaccag gctgtccttg acctgcagag  1140
atgtgtgagc ttggagccca agaacaaagt tttccaggag ccttgcgga acatcggggg  1200 ccagattcag gagaaggtgc gatacatgtc ctcgacggat gccaaagtgg aacagatgtt  1260
tcagatactg ttggacccag aagagaaggg cactgagaaa aagcaaaagg cttctcagaa  1320
cctggtggtg ctgccaggg aggatgctgg agcgagaag atcttccgga gtaatgggt  1380 tcagctcttg caacgtttac tggacatggg agagactgac ctcatgctgg cggctctgcg  1440
tacgctggtt ggcatttgct ctgagcatca gtcacggaca gtggcaaccc tgagcatact  1500
gggaactcgg cgagtagtct ccatcctggg cgtggaaagc caggctgtgt ccctggctgc  1560
ctgccacctg ctgcaggtta tgtttgatgc cctcaaggaa ggtgtcaaaa aaggcttccg  1620

-continued

```
aggcaaagaa ggtgccatca ttgtggatcc tgcccgggag ctgaaggtcc tcatcagtaa    1680
cctcttagat ctgctgacag aggtgggggt ctctggccaa ggccgagaca atgccctgac    1740
cctcctgatt aaagcggtgc cccggaagtc tctcaaggac cccaacaaca gcctcaccct    1800
ctgggtcatc gaccaaggtc tgaaaaagat tttggaagtg gggggctctc tacaggaccc    1860
tcctggggag ctcgcagtga ccgcaaacag ccgcatgagc gcctctattc tcctcagcaa    1920
gctctttgat gacctcaagt gtgatgcgga gagggagaat ttccacagac tttgtgaaaa    1980
ctacatcaag agctggtttg agggccaagg gctggccggg aagctacggg ccatccagac    2040
ggtgtcctgc ctcctgcagg gcccatgtga cgctggcaac cgggccttgg agctgagcgg    2100
tgtcatggag agtgtgattg ctctgtgtgc ctctgagcag gaggaggagc agctggtggc    2160
cgtggaggct ctgatccatg cagccggcaa ggctaagcgg gcctcattca tcactgccaa    2220
tggtgtctcg ctgctgaagg acctatataa gtgcagcgag aaggacagca tccgcatccg    2280
ggcgctagtg ggactctgta agctcggttc ggctggaggg actgacttca gcatgaagca    2340
gtttgctgaa ggctccactc tcaaactggc taagcagtgt cgaaagtggc tgtgcaatga    2400
ccagatcgac gcaggcactc ggcgctgggc agtggagggc ctggcttacc tgaccttga    2460 tgccgacgtg aaggaagagt ttgtggagga tgcggctgct ctgaaagctc tgttccagct    2520
cagcaggttg gaggagaggt cagtgctctt tgcggtggcc tcagcgctgg tgaactgcac    2580
caacagctat gactacgagg agcccgaccc caagatggtg gagctggcca gtatgccaa    2640 gcagcatgtg cccgagcagc accccaagga caagccaagc ttcgtgcggg ctcgggtgaa    2700
gaagctgctg gcagcgggtg tggtgtcggc catggtgtgc atggtgaaga cggagagccc    2760
tgtgctgacc agttcctgca gagagctgct ctccagggtc ttcttggctt tagtggaaga    2820
ggtagaggac cgaggcactg tggttgccca gggaggcggc agggcgctga tcccgctggc    2880
cctggaaggc acgacgtgg ggcagacaaa ggcagcccag gcccttgcca agctcaccat    2940
cacctccaac ccggagatga ccttccctgg cgagcggatc tatgaggtgg tccggccct    3000 cgtctccctg ttgcacctca actgctcagg cctgcagaac ttcgaggcgc tcatggccct    3060
aacaaacctg gctgggatca gcgagaggct ccggcagaag atcctgaagg agaaggctgt    3120
gcccatgata gaaggctaca tgtttgagga gcatgagatg atccgccggg cagccacgga    3180
gtgcatgtgt aacttggcca tgagcaagga ggtgcaggac ctcttcgaag cccagggcaa    3240
tgaccgactg aagctgctgg tgctgtacag tggagaggat gatgagctgc tacagcgggc    3300
agctgccggg ggcttggcca tgcttacctc catgcgcccc acgctctgca gccgcattcc    3360
ccaagtgacc acacactggc tggagatcct gcaggccctg cttctgagct ccaaccagga    3420
gctgcagcac cggggtgctg tggtggtgct gaacatggtg gaggcctcga gggagattgc    3480
cagcaccctg atggagagtg agatgatgga gatcttgtca gtgctagcta agggtgacca    3540
cagccctgtc acaagggctg ctgcagcctg cctggacaaa gcagtggaat atgggcttat    3600
ccaacccaac caagatggag agtga                                          3625
```

<210> SEQ ID NO 24
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 24

```
caccgtgagt ggtccaggga cccccgaag ggggtccctg gaccactcac        50

<210> SEQ ID NO 25
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 25
aaaagtgagt ggtccaggga ccccttcgg ggggtccctg gaccactcac        50

<210> SEQ ID NO 26
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 26
caccggacag aggtggtagt gaactcgaaa gttcactacc acctctgtcc        50

<210> SEQ ID NO 27
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 27
aaaaggacag aggtggtagt gaactttcga gttcactacc acctctgtcc        50
```

The invention claimed is:

1. A short interfering RNA (siRNA) or a short hairpin RNA (shRNA) molecule for targeting human UNC-45A splice variant in a cell that is substantially complementary to a nucleotide sequence of TGGCCGTCACTACCCTGGTTTCTTT (SEQ ID NO:5) or GGACAGAGGTGGTAGTGAACT (SEQ ID NO:6) of the UNC-45A929 splice variant, or a nucleotide sequence of GGTCCAGGGACCCCCGAGCCCCG (SEQ ID NO:7) or GTGAGTGGTCCAGGGACCCC (SEQ ID NO:8) of UNC-45A944.

2. The RNA of claim 1, wherein the siRNA comprises one or more modified nucleotides.

3. The RNA of claim 1, wherein the shRNA is expressed from a vector.

4. A method of reducing the proliferation of a cancer cell, the method comprising contacting the cancer cell with an RNAi agent of claim 1 that specifically downregulates the expression of UNC-45A splice variants.

5. The method of claim 4, wherein the RNAi agent is a siRNA molecule that specifically targets UNC-45A929 splice variant.

6. The method of claim 4, wherein the RNAi agent is a shRNA molecule.

7. The method of claim 4, wherein the cancer cell is selected from the group consisting of breast cancer, cervical cancer and colon cancer.

8. The method of claim 4, wherein the cancer cell is a metastatic breast cancer cell.

9. The method of claim 4, wherein the RNAi agent is a siRNA molecule that targets TGGCCGTCACTACCCTGGTTTCTTT (SEQ ID NO:5) or GGACAGAGGTGGTAGTGAACT (SEQ ID NO:6) of the UNC-45A929 splice variant.

10. A short interfering RNA (siRNA) or a short hairpin RNA (shRNA) molecule for targeting human UNC-45A splice variant in a cell that is fully complementary to nucleotide sequence of TGGCCGTCACTACCCTGGTTTCTTT (SEQ ID NO:5) or GGACAGAGGTGGTAGTGAACT (SEQ ID NO:6) of the UNC-45A929 splice variant, or nucleotide sequence of GGTCCAGGGACCCCCGAGCCCCG (SEQ ID NO:7) or GTGAGTGGTCCAGGGACCCC (SEQ ID NO:8) of UNC-45A944.

* * * * *